United States Patent
White

[11] 3,974,146
[45] Aug. 10, 1976

[54] CYANOLPOXY INTERMEDIATES FOR PROSTAGLANDINS AND PROCESS FOR PREPARING SAME

[75] Inventor: David R. White, Kalamazoo, Mich.
[73] Assignee: The Upjohn Company, Kalamazoo, Mich.
[22] Filed: Apr. 9, 1975
[21] Appl. No.: 566,356

[52] U.S. Cl. .................... 260/240 R; 260/343.3 R; 260/348 R
[51] Int. Cl.² ............... C07C 177/00; C07D 307/77
[58] Field of Search .......... 260/348 R, 343.3, 240 R

[56] References Cited
UNITED STATES PATENTS

| | | | |
|---|---|---|---|
| 2,070,990 | 2/1937 | Groll et al. | 260/348 R |
| 2,772,295 | 11/1956 | Burness | 260/348 R X |
| 3,462,462 | 8/1969 | Hatch | 260/348 R |
| 3,711,515 | 1/1973 | Kelly | 260/343.3 |
| 3,864,387 | 2/1975 | Nelson | 260/343.3 X |

OTHER PUBLICATIONS
Manuel Bollester; "Mechanisms of the Darzens and Related Cordensations," in Chem. Rev. 55–No. 2, 283–300, 1955.

Primary Examiner—Allen B. Curtis
Attorney, Agent, or Firm—Morris L. Nielsen

[57] ABSTRACT
Tricyclic cyanoepoxides of the formula

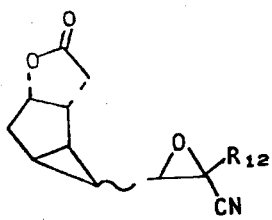

wherein $R_{12}$ is

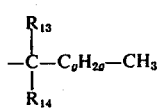 (1)

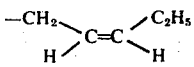

(2)

or

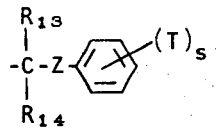 (3)

wherein $C_gH_{2g}$, $R_{13}$, $R_{14}$, s, T, Z, and ~ are as defined hereinafter;

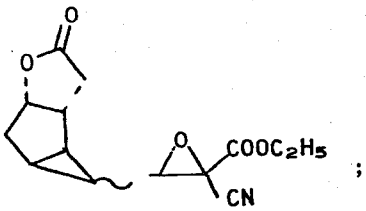

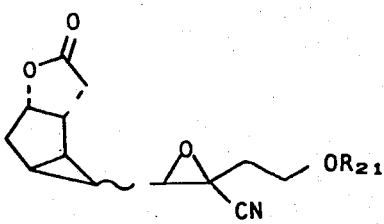

wherein $R_{21}$ is a blocking group as defined hereinafter; and

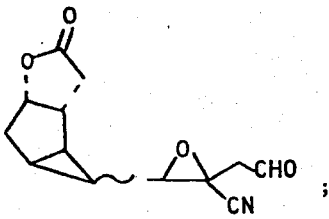

together with processes for preparing them. The cyanoepoxides are useful intermediates in preparing prostaglandins and prostaglandin analogs having pharmacological utility.

32 Claims, No Drawings

CYANOLPOXY INTERMEDIATES FOR PROSTAGLANDINS AND PROCESS FOR PREPARING SAME

BACKGROUND OF THE INVENTION

This invention relates to intermediates useful in the preparation of prostaglandins and to a process for preparing them.

Each of the known prostaglandins is a derivative of prostanoic acid which has the following structure and atom numbering:

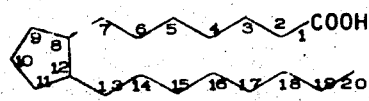

A systematic name for prostanoic acid is 7-[(2β-octyl)-cyclopent-1α-yl]heptanoic acid.

Prostaglandin $E_2$, "$PGE_2$", has the following structure:

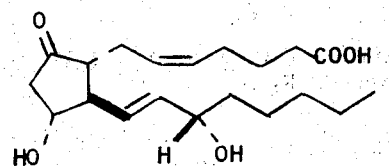

Prostaglandin $F_{2\alpha}$, "$PGF_{2\alpha}$", has the following structure:

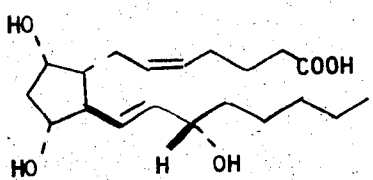

The prostaglandin formulas mentioned above each have several centers of asymmetry. Each formula represents a molecule of the particular optically active form of the prostaglandin obtained from certain mammalian tissues, for example, sheep vesicular glands, swine lung, and human seminal plasma, or by reduction or dehydration of a prostaglandin so obtained. See, for example, Bergstrom et al., Pharmacol. Rev. 20, 1 (1968), and references cited therein. The mirror image of each formula represents a molecule of the other enantiomeric form of that prostaglandin. The racemic form of the prostaglandins consists of equal numbers of two types of molecules, one represented by one of the above formulas and the other represented by the mirror image of that formula. Thus, both formulas are needed to define a racemic prostaglandin. See Nature 212, 38 (1966) for discussion of the stereochemistry of the prostaglandins.

In the formulas above, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e. above the plane of the cyclopentane ring. In the formulas above, the hydroxyl attachment to carbon 15 is in the alpha configuration, as indicated by the broken line. In formulas below, this convention is also used for intermediates having hydroxyl substituted at the corresponding position on the side chain. A wavy line ∼ indicates optional attachment to carbon 15 in either alpha or beta configuration.

The various optically active and racemic prostaglandins and their alkyl esters are useful for various pharmacological purposes. With particular regard to $PGF_{2\alpha}$ see, for example, Bergstrom et al., Pharmacol. Rev. 20, 1 (1968), and references cited therein, Wiqvist et al., The Lancet, 889 (1970), and Karim et al., J. Obstet. Gynaec. Brit. Cwlth., 76, 769 (1969). As to the other prostaglandins, see, for example Ramwell et al., Nature 221, 1251 (1969).

Previously, the preparation of an intermediate bicyclic lactone ketone of the formula

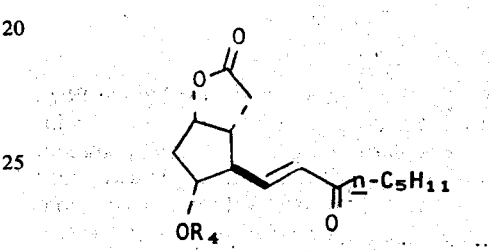

wherein $R_4$ is acetyl was reported by E. J. Corey et al., J. Am. Chem. Soc. 91, 5675 (1969), and later disclosed in an optically active form by E. J. Corey et al., J. Am. Chem. Soc. 92, 397 (1970). Conversion of this intermediate to $PGE_2$ and $PGF_{2\alpha}$, either in racemic (dl-) or optically active form, was disclosed in those publications. For that compound wherein $R_4$ is benzoyl see U.S. Pat. No. 3,778,450.

Related compounds of the formula

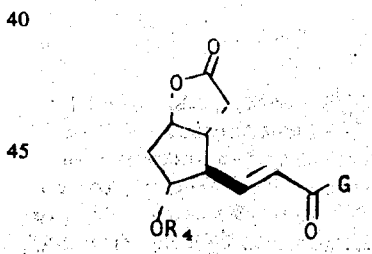

wherein $R_4$ is acetyl or benzoyl have been disclosed as follows:

1. wherein G is alkyl of one to 10 carbon atoms, inclusive, substituted with zero to 3 fluoro, German Offenlegungsschrift No. 2,406,287, Derwent Farmdoc 60337V;
2. wherein G is

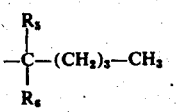

wherein $R_5$ and $R_6$ are hydrogen, methyl, or ethyl, provided that at least one of $R_5$ and $R_6$ is not hydrogen, German Offenlegungsschrift No. 2,217,044, Derwent Farmdoc 71483T;
3. wherein G is

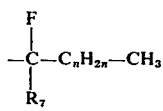

wherein $C_nH_{2n}$ is alkylene of one to 9 carbon atoms, inclusive, with one to 6 carbon atoms, inclusive, in the chain between —$CFR_7$— and terminal methyl and wherein $R_7$ is hydrogen, methyl, ethyl, or fluoro, Netherlands Application No. 7305817, Derwent Farmdoc 69717U; and 4. wherein G is

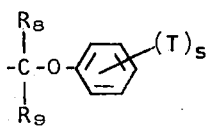

wherein $R_8$ and $R_9$ are hydrogen, methyl, or ethyl, wherein T is alkyl of one to 3 carbon atoms, inclusive, fluoro, chloro, trifluoro, or —$OR_{10}$ wherein $R_{10}$ is alkyl of 1 to 3 carbon atoms, inclusive, and wherein $s$ is zero, 1, 2, or 3, with the proviso that not more than two T's are other than alkyl, Netherlands Application No. 7306462, Derwent Farmdoc 73279U.

Also disclosed is a compound of the formula:

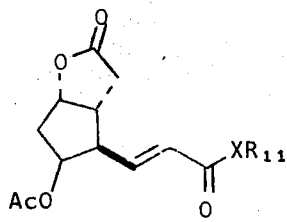

III wherein Ac represents an acyl radical, either acetyl or p-phenylbenzoyl, X is an alkylene radical of 2 or 3 carbon atoms, optionally bearing as substituent or substituents one or two alkyl radicals each of 1 to 4 carbon atoms, and $R_{11}$ is an aryl or thienyl radical, which is unsubstituted or which is substituted by halogen atoms, nitro radicals, alkyl, halogenoalkyl or alkoxy radicals each of 1 to 3 carbon atoms or dialkylamino radicals wherein each alkyl is of 1 to 3 carbon atoms, Netherlands Application No. 7209817, Derwent Farmdoc 5789U.

A related disclosed compound is

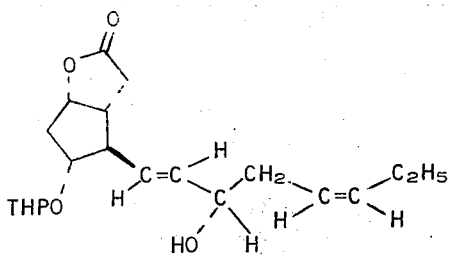

IV wherein THP is tetrahydropyranyl, useful in the synthesis of $PGF_{3\alpha}$, E. J. Corey et al. J. Am. Chem. Soc. 93, 1490 (1971).

SUMMARY OF THE INVENTION

It is the purpose of this invention to provide novel intermediates useful in the preparation of prostaglandins commercially in substantial amount, with high purity, and at reasonable cost. It is a further purpose to provide processes for preparing these intermediates and for utilizing them.

Thus there is provided a process for preparing an optically active bicyclic lactone ketone of the formula

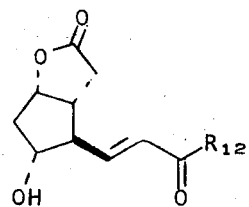

V or a mixture of that compound and the enantiomer thereof, wherein $R_{12}$ is

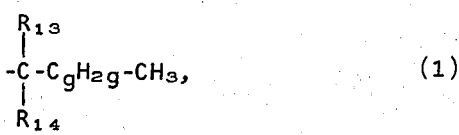 (1)

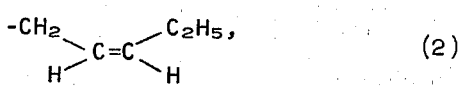 (2)

or 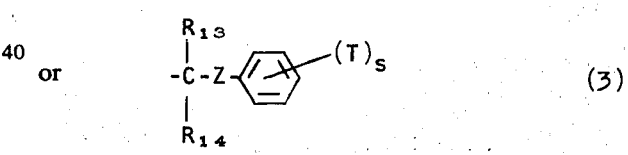 (3)

wherein $C_gH_{2g}$ is alkylene of one to 9 carbon atoms, inclusive, with one to 5 carbon atoms, inclusive, in the chain between —$CR_{13}R_{14}$— and terminal methyl; wherein $R_{13}$ and $R_{14}$ are hydrogen, alkyl of 1 to 4 carbon atoms, inclusive, or fluoro, being the same or different, with the proviso that $R_{13}$ is fluoro only when $R_{14}$ is hydrogen or fluoro; wherein T is alkyl of 1 to 4 carbon atoms, inclusive, fluoro, chloro, trifluoromethyl, or —$OR_{15}$, wherein $R_{15}$ is hydrogen or alkyl of 1 to 4 carbon atoms, inclusive, and $s$ is zero, 1, 2, or 3, with the proviso that not more than two T's are other than alkyl; and wherein Z represents an oxa atom (—O—) or $C_jH_{2j}$, wherein $C_jH_{2j}$ is a valence bond or alkylene of one to 9 carbon atoms, inclusive, substituted with zero, one, or 2 fluoro, with 1 to 6 carbon atoms, inclusive, between —$CR_{13}R_{14}$— and the ring; which comprises a. starting with a tricyclic lactone aldehyde of the formula

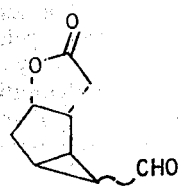

VI or a mixture of that compound and the enantiomer thereof, wherein ~ indicates attachment to the cyclopropane ring in endo or exo configuration, and reacting said aldehyde with a nitrile of the formula

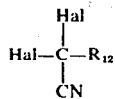

wherein Hal is chloro, bromo, or iodo, the two Hal's being the same or different, and wherein $R_{12}$ is defined as above, to form an optically active cyanoepoxide of the formula

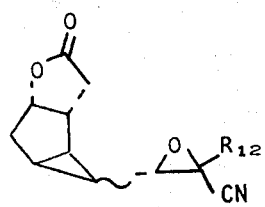

VII or a mixture of that compound and the enantiomer thereof, wherein $R_{12}$ and ~ are as defined above;

b. reacting said cyanoepoxide with formic acid to produce an optically active cyanohydrin monoformate of the formula

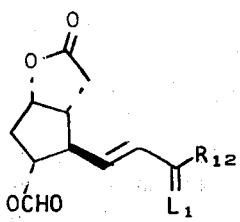

VIII or a mixture of that compound and the enantiomer thereof, wherein $R_{12}$ is as defined above and wherein $L_1$ represents either

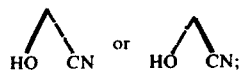

and c. transforming the product of step (b) to said bicyclic lactone ketone by d. removing hydrocyanic acid by dehydrocyanation to convert the

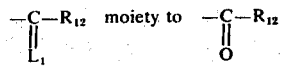

and e. replacing formyl with hydroxyl, said steps (d) and (e) being performed either in the order (d)–(e) or (e)–(d).

There is further provided a process for preparing an optically active bicyclic lactone ketone of the formula

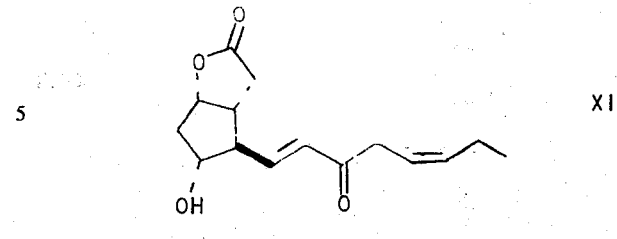

XI or a mixture of that compound and the enantiomer thereof, which comprises a. starting with a tricyclic lactone cyanoepoxide of the formula

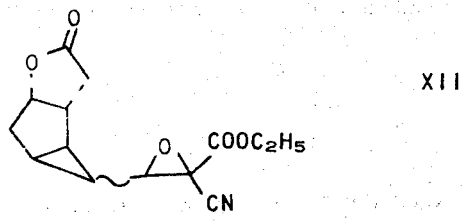

XII or a mixture of that compound and the enantiomer thereof, wherein ~ indicates attachment to the cyclopropane ring in endo or exo configuration, and reacting said cyanoepoxide with formic acid to produce an optically active cyanohydrin monoformate of the formula

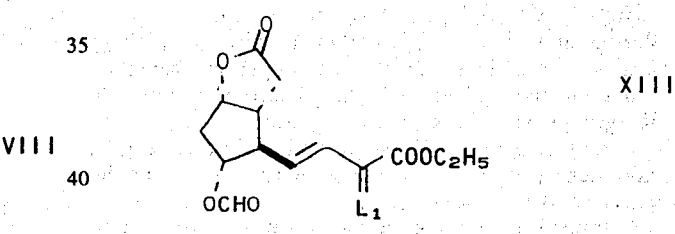

XIII or a mixture of that compound and the enantiomer thereof, wherein $L_1$ represents either

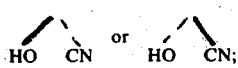

b. replacing formyl with hydroxyl to produce an optically active cyanohydrin of the formula

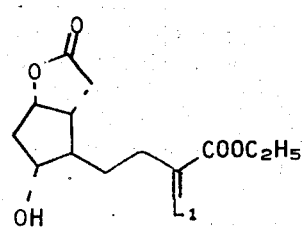

XIV or a mixture of that compound and the enantiomer thereof, wherein $L_1$ is as defined above;

c. transforming the product of step (b) to form a diether of the formula

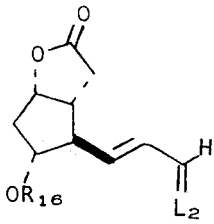

XVII or a mixture of that compound and the enantiomer thereof, wherein $L_2$ represents either

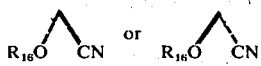

and wherein $R_{16}$ is 1-ethoxyethyl, tetrahydropyranyl, tetrahydrofuranyl, or a group of the formula

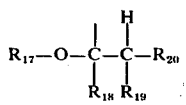

wherein $R_{17}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of 1 to 4 carbon atoms, inclusive, wherein $R_{18}$ and $R_{19}$ are the same or different, being hydrogen, alkyl of 1 to 4 carbon atoms, inclusive, phenyl or phenyl substituted with one, 2, or 3 alkyl of 1 to 4 carbon atoms, inclusive, or, when $R_{18}$ and $R_{19}$ are taken together, $-(CH_2)_a-$ or $-(CH_2)_b-O-(CH_2)_c-$ wherein $a$ is 3, 4, or 5, $b$ is 1, 2, or 3, and $c$ is 1, 2, or 3 with the proviso that $b$ plus $c$ is 2, 3, or 4, and wherein $R_{20}$ is hydrogen or phenyl; by d. replacing the hydrogen of the hydroxyl groups with $R_{16}$ groups wherein $R_{16}$ is as defined above, and e. replacing the $-COOC_2H_5$ moiety with hydrogen, said steps (d) and (e) being performed either in the order (d)–(e) or (e)–(d);

f. transforming the product of step (c) to a compound of the formula

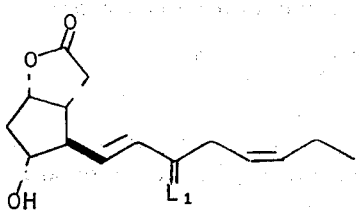

XVIII or a mixture of that compound and the enantiomer thereof, wherein $L_1$ is as defined above, by the steps of deprotonating, alkylating with 1-bromo-cis-2-pentene, and deblocking, and g. removing hydrocyanic acid by dehydrocyanation to convert the

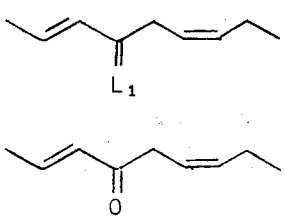 moiety to

There is further provided a process for preparing an optically active bicyclic lactone ketone of the formula

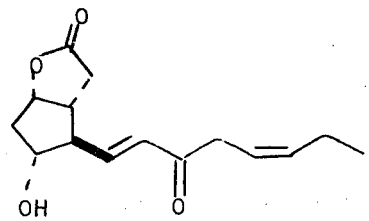

XI or a mixture of that compound and the enantiomer thereof, which comprises a. starting with a tricyclic lactone aldehyde of the formula

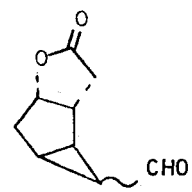

VI or a mixture of that compound and the enantiomer thereof, wherein ~ indicates attachment to the cyclopropane ring in endo or exo configuration, and reacting said aldehyde with a nitrile of the formula

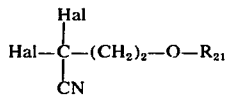

wherein Hal is chloro, bromo, or iodo, the two Hal's being the same or different, and wherein $R_{21}$ is (1) $R_{16}$, defined as 1-ethoxyethyl, tetrahydropyranyl, tetrahydrofuranyl, or a group of the formula

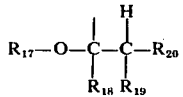

wherein $R_{17}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of 1 to 4 carbon atoms, inclusive, wherein $R_{18}$ and $R_{19}$ are the same or different, being hydrogen, alkyl of 1 to 4 carbon atoms, inclusive, phenyl or phenyl substituted with one, 2, or 3 alkyl of 1 to 4 carbon atoms, inclusive, or, when $R_{18}$ and $R_{19}$ are taken together, $-(CH_2)_a-$ or $-(CH_2)_b-O-(CH_2)_c-$ wherein $a$ is 3, 4, or 5, $b$ is 1, 2, or 3, and $c$ is 1, 2, or 3 with the proviso that $b$ plus $c$ is 2, 3, or 4, and wherein $R_{20}$ is hydrogen or phenyl; or (2) carboxyacyl $-C(O)R_{22}$ wherein $R_{22}$ is hydrogen or alkyl of 1 to 17 carbon atoms, inclusive, to form an optically active cyanoepoxide of the formula

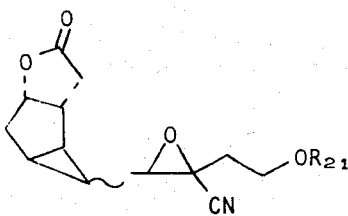

XIX or a mixture of that compound and the enantiomer thereof, wherein $R_{21}$ and ~ are as defined above;

b. transforming the product of step (a) to a compound of the formula

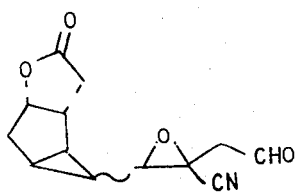

XX or a mixture of that compound and the enantiomer thereof, wherein ~ is as defined above, by hydrolyzing $-CH_2CH_2-O-R_{21}$ to $-CH_2CH_2-OH$ and thereafter oxidizing $-CH_2CH_2-OH$ to $-CH_2CHO$;

c. transforming the product of step (b) to a cyanoepoxide of the formula

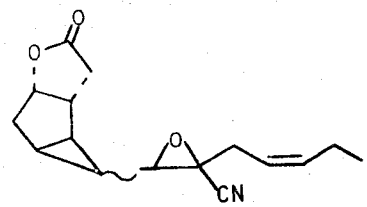

XXI or a mixture of that compound and the enantiomer thereof, wherein ~ is as defined above;

d. reacting said cyanoepoxide with formic acid to produce an optically active cyanohydrin monoformate of the formula

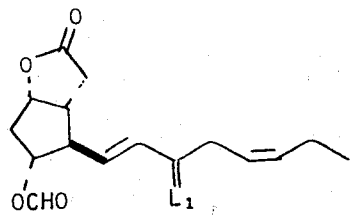

XXII or a mixture of that compound and the enantiomer thereof, wherein $L_1$ represents either

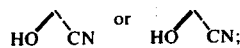

and e. transforming the product of step (d) to said bicyclic lactone ketone by f. removing hydrocyanic acid by dehydrocyanation to convert the

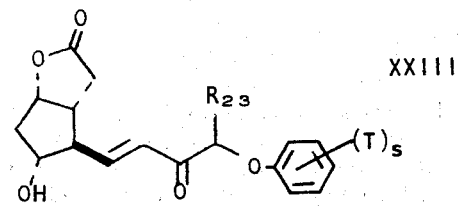

moiety to and g. replacing formyl with hydroxyl, said steps (f) and (g) being performed either in the order (f)–(g) or (g)–(f).

There is further provided a process for preparing an optically active bicyclic lactone ketone of the formula

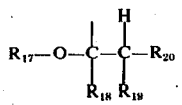

XXIII or a mixture of that compound and the enantiomer thereof, wherein T is alkyl of one to 4 carbon atoms, inclusive, fluoro, chloro, trifluoromethyl, or $-OR_{15}$, wherein $R_{15}$ is hydrogen or alkyl of 1 to 4 carbon atoms, inclusive, and s is zero, 1, 2, or 3, with the proviso that not more than two T's are other than alkyl and when s is 2 or 3 the T's are either the same or different; and wherein $R_{23}$ is hydrogen or alkyl of 1 to 4 carbon atoms, inclusive; which comprises a. starting with a bicyclic lactone cyanohydrin diether of the formula

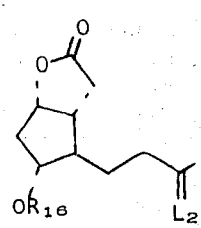

XVII or a mixture of that compound and the enantiomer thereof, wherein $R_{16}$ is 1-ethoxyethyl, tetrahydropyranyl, tetrahydrofuranyl, or a group of the formula $$R_{17}-O-\underset{R_{18}}{\overset{H}{C}}-\underset{R_{19}}{\overset{H}{C}}-R_{20}$$

wherein $R_{17}$ is alkyl of 1 to 17 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of 1 to 4 carbon atoms, inclusive, wherein $R_{18}$ and $R_{19}$ are the same or different, being hydrogen, alkyl of 1 to 4 carbon atoms, inclusive, phenyl or phenyl substituted with one, 2, or 3 alkyl of 1 to 4 carbon atoms, inclusive, or, when $R_{18}$ and $R_{19}$ are taken together, —$(CH_2)_a$— or —$(CH_2)_b$—O—$(CH_2)_c$— wherein $a$ is 3, 4, or 5, $b$ is 1, 2, or 3, and $c$ is 1, 2, or 3 with the proviso that $b$ plus $c$ is 2, 3, or 4, and wherein $R_{20}$ is hydrogen or phenyl; and wherein $L_2$ represents either

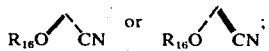

and transforming said diether into an alkoxide of the formula

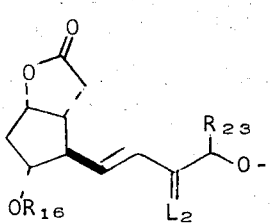

XXIV wherein $R_{23}$ is hydrogen or alkyl of one to 4 carbon atoms, inclusive, and wherein $R_{16}$ and $L_2$ are as defined above, by successively deprotonating and reacting the carbanion of said diether with an aldehyde of the formula $R_{23}$—CHO wherein $R_{23}$ is as defined above b. arylating the product of step (a) to form a compound of the formula

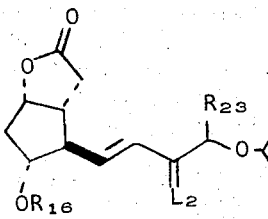

XXV or a mixture of that compound and the eantiomer thereof, wherein $R_{16}$, $R_{23}$, $s$, T, and $L_2$ are as defined above;

c. replacing the $R_{16}$ groups with hydrogen; and
d. removing hydrocyanic acid by dehydrocyanation to convert the

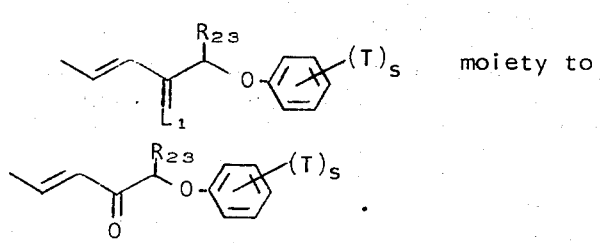

moiety to

Accordingly, from the above processes there are provided new intermediates corresponding to formulas VII, VIII, XII, XIV, XVII, XVIII, XIX, XX, XXI, XXII, XXIV, and XXV above, wherein $R_{12}$, $R_{16}$, $R_{21}$, $R_{23}$, $s$, T, $L_1$, $L_2$, and are as defined above.

With regard to formulas V to XXVI herein, alkyl groups of 1 to 4 carbon atoms, inclusive, include methyl, ethyl, propyl, butyl, and isomeric forms thereof. Alkyl groups of 1 to 17 carbon atoms, inclusive, include those given above, and pentyl, hexyl, heptyl, octyl, nonyl, decyl, undecyl, dodecyl, tridecyl, tetradecyl, pentadecyl, hexadecyl, heptadecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are (o-, m-, or p-)chlorophenyl, 2,4-diclorophenyl, 2,4,6-trichlorophenyl, (o-, m-, or p-)tolyl, p-ethylphenyl, p-tert-butylphenyl, 2,5-dimethylphenyl, 4-chloro-2-methylphenyl, and 2,4-dichloro-3-methylphenyl.

Examples of alkylene of 1 to 9 carbon atoms, inclusive, with 1 to 5 carbon atoms inclusive, in the chain, within the scope of $C_gH_{2g}$ as defined above, are methylene, ethylene, trimethylene, tetramethylene, and pentamethylene, and those alkylene with one or more alkyl substituents on one or more carbon atoms thereof, e.g. —$CH(CH_3)$—, —$C(CH_3)_2$—, —$CH(CH_2CH_3)$—, —$CH_2$—$CH(CH_3)$—, —$CH(CH_3)$—$CH(CH_3)$—, —$CH_2$—$C(CH_3)_2$—, —$CH_2$—$CH(CH_3)$—$CH_3$—, —$CH_2$—$CH_2$—$CH(CH_2CH_2CH_3)$—, —$CH(CH_3)$—$CH(CH_3)$—$CH_2$—$CH_2$—, —$CH_2$—$CH_2$—$CH_2$—$C(CH_3)_2$—$CH_2$, and —$CH_2$—$CH_2$—$CH_2$—$CH_2$—$CH(CH_3)$—. Examples of alkylene of 1 to 9 carbon atoms, inclusive, substituted with zero, one, or 2 fluoro, with 1 to 6 carbon atoms in the chain, within the scope of the $C_jH_{2j}$ as defined above, are those given above for $C_gH_{2g}$ and hexamethylene, including hexamethylene with one or more alkyl substituents on 1 or more carbon atoms thereof, and including those alkylene groups with one or 2 fluoro substituents on 1 or 2 carbon atoms thereof, e.g. —$CHF$—$CH_2$—, —$CHF$—$CHF$—, —$CH_2$—$CH_2$—$CF_2$—, —$CH_2$—$CHF$—$CH_2$—, —$CH_2$—$CH_2$—$CF(CH_3)$—, —$CH_2$—$CH_2$—$CF_2$—$CH_2$—, —$CH(CH_3)$—$CH_2$—$CH_2$—$CHF$—, —$CH_2$—$CH_2$—$CH_2$—$CH_2$—$CF_2$—, —$CHF$—$CH_2$—$CH_2$—$CH_2$—$CH_2$—$CHF$—, —$CF_2$—$CH_2$—$CH_2$—$CH_2$—$CH_2$—, —$CH_2$—$CH_2$—$CH_2$—$CF_2$—$CH_2$—$CH_2$—, and —$CH_2$—$CH_2$—$CH_2$—$CH_2$—$CH_2$—$CF_2$.

Examples of

as defined above are phenyl, (o-, m-, or p-)tolyl, (o-, m-, or p-)ethylphenyl, (o-, m-, or p-)propylphenyl, (o-, m-, or p-)butylphenyl, (o, m-, or p-)isobutylphenyl, (o-, m-, or p-)tert-butylphenyl, 2,3-xylyl, 2,4-xylyl, 2,5-xylyl, 2,6-xylyl, 3,4-xylyl, 2,6-diethylphenyl, 2-ethyl-p-tolyl, 4-ethyl-o-tolyl, 5-ethyl-m-tolyl, 2-propyl-(o-, m-, or p-)tolyl, 4-butyl-m-tolyl, 6-tert-butyl-m-tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)-chlorophenyl, 2-chloro-p-tolyl, (3-, 4-, 5-, or 6-)choloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3-, or 4-)chloro-2-fluorophenyl, α, α, α-trifluoro-(o-, m-, or p-)-tolyl, (o-, m-, or p-)methoxyphenyl, (o-, m-, or p-)ethoxyphenyl, (4 - or 5-)chloro-2-methoxyphenyl, and 2,4-dichloro-(5- or 6-)methoxyphenyl.

The processes described herein and the intermediates produced in the course of those processes lead to bicyclic lactone ketones V, XI, and XXIII which are usefl in preparing prostaglandins or prostaglandin analogs having pharmacological activity. See the references cited above under "Background of the Invention".

The processes are useful for preparing said ketones within the scope of the substituent groups $R_{12}$, $R_{23}$, and T as defined herein. However, certain of said ketones are preferred for the reason that they are especially useful in preparing prostaglandins or prostaglandin analogs having especially desirable biological response specificity, potency, and duration of activity, as well as advantageous qualities for administration by oral, sublingual, intravaginal, buccal or rectal methods.

For example, considering ketone V, wherein $R_{12}$ is

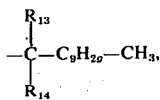

it is preferred that $C_gH_{2g}$ be ethylene, trimethylene, or tetramethylene, and that $R_{13}$ and $R_{14}$ be hydrogen or methyl or that both $R_{13}$ and $R_{14}$ be methyl or fluoro. When $R_{12}$ in ketone V is

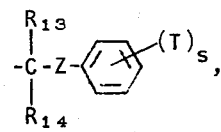

and when Z is -oxa- (as also in ketone XXIII) it is preferred that $R_{13}$ and $R_{14}$ be hydrogen or methyl, that s be zero or 1, and that T be methyl, fluoro, chloro, trifluoromethyl, or methoxy; when Z is $C_jH_{2j}$, it is preferred that $C_jH_{2j}$ be a valence bond or a chain of 1 to 3 carbon atoms, that $R_{13}$ and $R_{14}$ be hydrogen or methyl, or that both $R_{13}$ and $R_{14}$ be methyl or fluoro, that s be zero or 1, and that T be methyl, fluoro, chloro, trifluoromethyl, or methoxy. In ketone XXIII it is preferred that $R_{23}$ be hydrogen or methyl.

CHART A

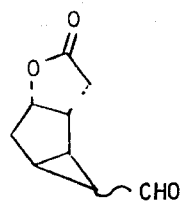

VI

↓ step a

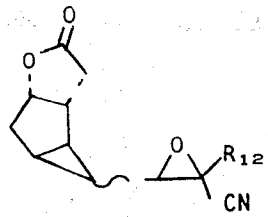

VII

↓ step b

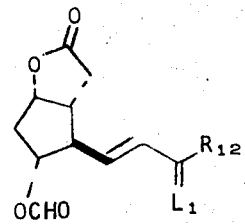

VIII

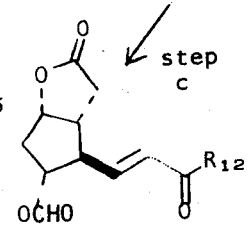    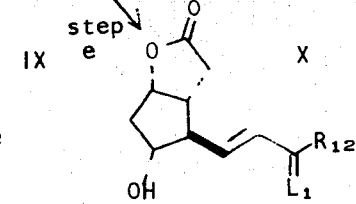

↙ step c    IX    ↘ step e    X

↘ step d    ↙ step f

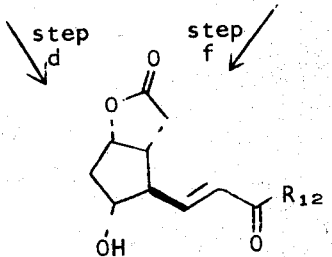

V

CHART B

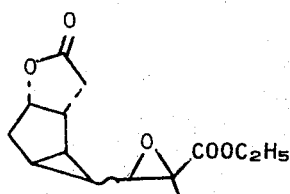

XII

↓ step j

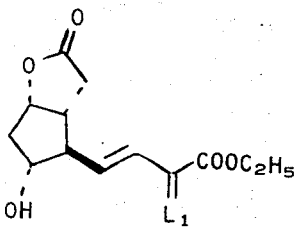

XIV

↙ step k    ↘ step m 3,974,146
CHART B (continued)
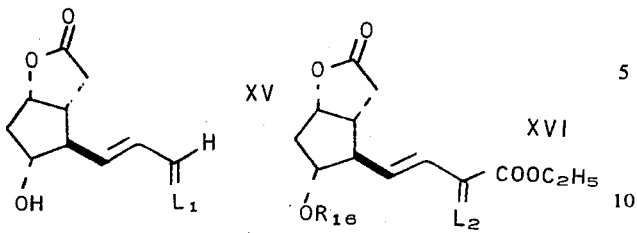
XV    XVI
step l ↓   ↓ step n
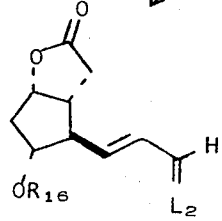
XVII
↓ step p
↓ step p
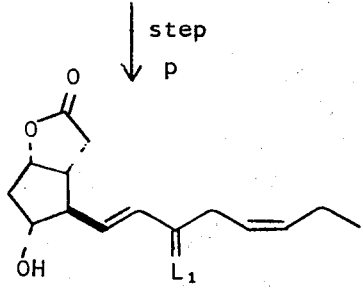
XVIII
↓ step q
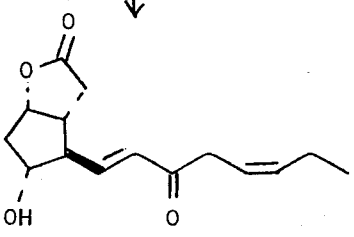
XI
CHART C
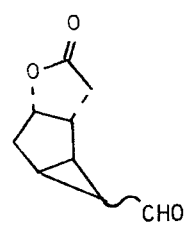
VI
↓ step r
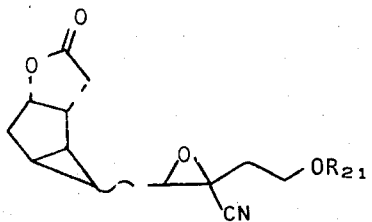
XIX
↓ step s
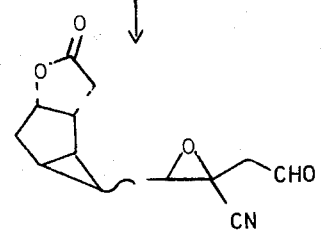
XX
↓ step t
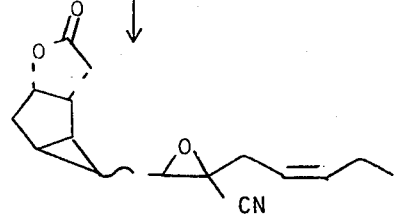
XXI
↓ step u
↓ step u
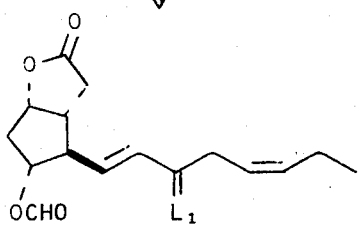
XXII
↓ step v
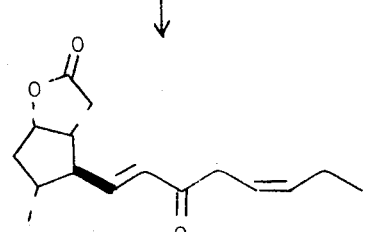
XI

CHART D

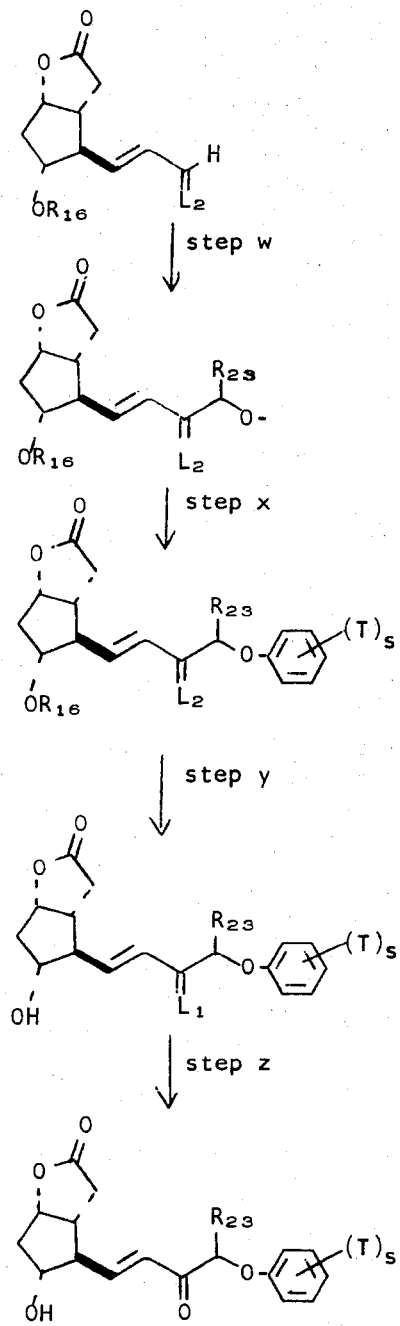

Reference to Charts A, B, C, and D will make clear the steps by which these processes are performed and by which these compounds are obtained. In these charts, $R_{12}$, $R_{16}$, $R_{21}$, $R_{23}$, $s$, $T$, $L_1$, $L_2$, and $\sim$ are as defined above, namely: $R_{12}$ is

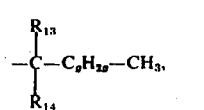 (1)

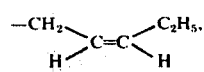 (2)

or (3) 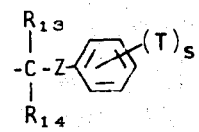

wherein $C_qH_{2q}$ is alkylene of one to 9 carbon atoms, inclusive, with one to 5 carbon atoms, inclusive, in the chain between —$CR_{13}R_{14}$— and terminal methyl; wherein $R_{13}$ and $R_{14}$ are hydrogen, alkyl of 1 to 4 carbon atoms, inclusive, or fluoro, being the same or different, with the proviso that $R_{13}$ is fluoro only when $R_{14}$ is hydrogen or fluoro; wherein T is alkyl of 1 to 4 carbon atoms, inclusive, fluoro, chloro, trifluoromethyl, or —$OR_{15}$, wherein $R_{15}$ is hydrogen or alkyl of 1 to 4 carbon atoms, inclusive, and $s$ is zero, 1, 2, or 3, with the proviso that not more than two T's are other than alkyl; and wherein Z represents an oxa atom (—O—) or $C_jH_{2j}$, wherein $C_jH_{2j}$ is a valence bond or alkylene of one to 9 carbon atoms, inclusive, substituted with zero, one, or 2 fluoro, with 1 to 6 carbon atoms, inclusive, betweeen —$CR_{13}R_{14}$— and the ring; $R_{16}$ is 1-ethoxyethyl, tetrahydropyranyl, tetrahydrofuranyl, or a group of the formula

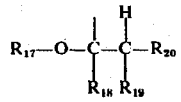

wherein $R_{17}$ is alkyl of one to 17 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of 1 to 4 carbon atoms, inclusive, or, when $R_{18}$ and $R_{19}$ are taken together, —$(CH_2)_a$— or —$(CH_2)_b$—O—$(CH_2)_c$— wherein $a$ is 3, 4, or 5, $b$ is 1, 2, or 3, and $c$ is 1, 2, or 3 with the proviso that $b$ plus $c$ is 2, 3, or 4, and wherein $R_{20}$ is hydrogen or phenyl; $R_{21}$ is (1) $R_{16}$ as defined above or (2) carboxyacyl —$C(O)R_{(O)R22}$ wherein $R_{22}$ is hydrogen or alkyl of 1 to 17 carbon atoms, inclusive; $R_{23}$ is hydrogen or alkyl of 1 to 4 carbon atoms, inclusive; $L_1$ represents

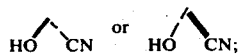

$L_2$ represents

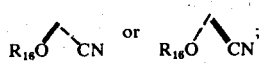

wherein $R_{16}$ is as defined above; and $\sim$ indicates attachment to the cyclopropane ring in endo or exo configuration.

The formulas as depicted herein are intended to represent those specific stereoisomers which will lead to prostaglandins or prostaglandin analog products having the same or similar pharmacological activity as corresponding prostaglandins obtained from natural sources. In Charts A–D the formulas as drawn represent specific optical isomers, following that convention. However, for purposes of convenience and brevity it is intended that such representations of the process steps for the optically active intermediates are also applicable to those same process steps as used for the corresponding racemic intermediates or mixtures of the enantiomeric forms of the intermediates.

Referring to Chart A, there are shown the steps by which tricyclic lactone aldehyde VI is transformed to bicyclic lactone ketone V. Starting material VI is readily available. See U.S. Pat. no. 3,816,462. That isomer is used which leads to prostaglandins having the same configuration as prostaglandins obtained from mammalian tissues: for example, for the endo form of aldehyde VI, m.p. 61°-64°C., $[\alpha]_D$ −30° (see R.C. Kelly et al., J. Am. Chem. Soc. 95, 2746 (1973)). Either the endo or exo form may be used. In step $a$ aldehyde VI is reacted with dihalonitrile of the formula

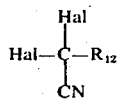

wherein Hal is chloro, bromo, or iodo, the two Hal's being the same or different, and wherein $R_{12}$ is defined above, to form cyanoepoxide VII.

The reagent dihalonitrile is available by methods known in the art, for example halogenation of a nitrile. Thus, 2,2-dibromoheptanenitrile is obtained by bromination of heptanenitrile. Alternately, a dihaloaldehyde is converted to the dihalonitrile by methods known in the art, following the sequence:

α,α-dihaloaldehyde
↓
α,α-dihaloacid
↓
α,α-dihaloacid chloride
↓
α,α-dihaloamide
↓
α,α-dihalonitrile Thus, 2,2-dibromo-4-phenyl-butanal is converted to 2,2-dibromo-4-phenylbutyronitrile,

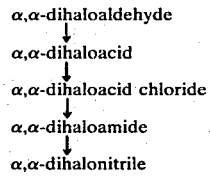

Similarly, 2,2-dibromo-cis-4-heptenal is converted to 2,2-dibromo-cis-4-heptenenitrile,

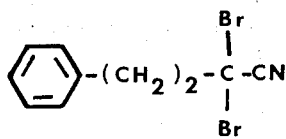

Examples of dihalonitriles useful for the purposes of this invention as depicted in Chart A are:

2,2-dibromohexanenitrile
2,2-dichlorooctanenitrile
2,2-diiodo-3-methylhexanenitirle
2,2-dibromo-3,3-dimethylheptanenitrile
2,2-diiodo-3-fluorooctanenitrile
2,2-dibromo-3,3-difluoroheptanenitrile
2,2-dibromo-cis-4-heptenenitrile
2,2-dibromo-3-phenylpropionitrile
2,2-dibromo-4-phenylbutyronitrile
2,2-dichloro-4-(4-chlorophenyl)butyronitrile
2,2-dibromo-4[(3-trifluoromethyl)phenyl]butyronitrile
2,2-diiodo-4-(2-fluorophenyl)butyronitrile
2,2-dibromo-4-(4-methoxypheny)butyronitrile
2,2-dibromo-3-phenoxypropionitrile.

In $a$, the reaction of aldehyde VI with the dihalonitrile is done in the presence of a reducing agent in an inert (aprotic) solvent such as tetrahydrofuran at about 0° to −15° C. For the reducing agent, trivalent phosphorus compounds are useful, including phosphines, phosphites, and phosphorous triamides. Particularly useful is hexamethylphosphorous triamide, $[(CH_3)_2N]_3P$. Certain metals or combinations of metals are also useful, including magnesium, strontium, barium, calcium, and zinc. The dihalonitrile and reducing agent are used in slight excess, 5–10% over the theoretical amounts based on aldehyde VI.

In step $b$, the cyanoepoxide VII is solvolyzed in substantially anhydrous formic acid at about 25° C. Advantageously the formic acid may be rendered anhydrous by contact with acetic anhydride prior to use. An inert solvent such as dichloromethane, benzene, or diethyl ether may be employed.

The product of step $b$ is converted to the formula-V ketone either by steps $c$–$d$ or $e$–$f$. In step $c$, hydrocyanic acid is removed by dehydrocyanation, employing a base such as an alkali metal carbonate, hydroxide or alkoxide, preferably potassium carbonate, at about 25° C. either in water or in an inert liquid medium such as tetrahydrofuran or benzene. In step $d$ the monoformate is hydrolyzed under either acidic or basic conditions, using aqueous mineral acids or sulfonic acids, for example p-toluenesulfonic acid, or aqueous weak bases such as alkali metal carbonates, bicarbonates, or phosphates, preferably sodium or potassium bicarbonate, together with a lower alkanol for improved solubility. For this hydrolysis, a temperature range of 10° to 50° C. is operable, preferably about 25° C.

In step $e$, the hydrolysis of the monoformate precedes the dehydrocyanation and for this hydrolysis acidic conditions are employed using aqueous mineral acids or sulfonic acids, preferably p-toluenesulfonic acid at about 10°–50° C., preferably about 25°C. Finally in step $f$ the dehydrocyanation is effected as in step $c$ above, for example with potassium carbonate in tetrahydrofuran or benzene or mixtures thereof at about 25° C.

In the processes of Chart A as well as Charts B, C, and D, the intermediate products are separated from the starting materials and impurities by methods described herein or known in the art, including partition extraction, fractional crystallization, and silica gel column chromatography. For convenience the product of an intermediate step may generally be used directly without isolation or purification.

Intermediates VII, VIII and X are obtained as various diastereomers or mixtures thereof. Although these may be separated by methods known in the art, for example by silica gel chromatography, such separation is generally not necessary for the purposes of this process as any or all of said diastereomers are useful for the purposes disclosed herein. Thus, from optically active aldehyde VI as starting material, the product V of Chart A is obtained in an optically active form. Similarly, from racemic aldehyde VI, product V is obtained as a racemic mixture.

Referring to Chart B, there are shown the steps by which cyanoepoxide XII is transformed into ketone XI. The starting material XII is prepared from aldehyde VI similarly to step *a* of Chart A but replacing the dihalonitrile reagent with the ethyl ester of dibromocyanoacetic acid:

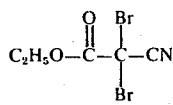

The reaction is carried out in an inert solvent in the presence of a reducing agent, preferably hexamethylphosphorous triamide, at about 0° to −15° C.

In step *j*, the cyanoepoxide XII is solvolyzed in formic acid as discussed above for step *a* of Chart A.

The product of step *j* is converted to cyanohydrin diether XVII either by steps *k–l* or *m–n*. In step *k*, carbethoxy cyanohydrin XIV is hydrolyzed to effectively cleave the ester and decarboxylate to compound XV. Dilute mineral acid and a miscible solvent such as tetrahydrofuran are used. In step *l* cyanohydrin XV is converted to diether XVII as follows.

When $R_{16}$ is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in slight excess, preferably 1.0 to 1.2 times theory. The reaction is carried out at about 20°–50° C.

When $R_{16}$ is of the formula

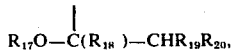

as defined above, the appropriate reagent is a vinyl ether, e.g. ethyl vinyl ether or any vinyl ether of the formula $R_{17}-O-C(R_{18})=CR_{19}R_{20}$ wherein $R_{17}$, $R_{18}$, $R_{19}$, and $R_{20}$ are as defined above; or an unsaturated cyclic or heteroocyclic compound, e.g. 1-cyclohexen-1-yl methyl ether

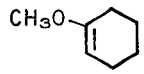

or 5,6-dihydro-4-methoxy-2H-pyran

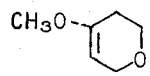

See C. B. Reese et al., J. Am. Chem. Soc. 89, 3366 (1967). The reaction conditions for such vinyl ethers and unsaturates are similar to those for dihydropyran above.

In step *m*, the etherification precedes the decarboxylation using the conditions and reagents for step *l* above. In step *n*, the conversion to compound XVII is done conveniently in dimethyl sulfoxide in the presence of sodium cyanide at temperatures above 120° C., preferably at about 160° C.

In step *p*, the three successive reactions of deprotonating, alkylating with 1-bromo-cis-2-pentene, and deblocking are carried out. Deprotonation to form a carbanion is done with an alkali metal amide, preferably lithium diisopropylamide, in an inert (aprotic) solvent such as tetrahydrofuran at below about −40° C. Alkylation occurs readily on addition of 1-bromo-cis-2-pentene. Deblocking (for example, replacement of 1-ethoxy-ethoxy groups with hydroxy) is done under mildly acidic conditions using for example aqueous organic acids such as acetic or citric acid at pH 2.0 at about 25°–30° C.

In step *q*, dehydrocyanation is achieved as for steps *c* and *f* in Chart A, for example by contacting the formula-XVIII compound with dilute aqueous sodium bicarbonate at about 25° C.

Referring to Chart C, there are shown the steps for an alternate process by which aldehyde VI is transformed into ketone XI. In this process the key intermediate XX is an aldehyde which is subjected to a Wittig alkylation at step *t* to extend the side chain.

In step *r*, aldehyde VI is reacted with a dihalobutyronitrile of the formula

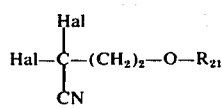

where $R_{21}$ is (1) $R_{16}$ as defined above or (2) carboxyacyl $-C(O)R_{22}$ wherein $R_{22}$ is hydrogen or alkyl of one to 17 carbon atoms, inclusive. Examples of the reagent are the 2,2-dibromo-4-hydroxybutyronitrile ester of acetic acid:

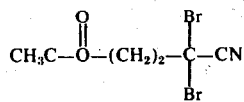

and the 1-ethoxyethyl ether of 2,2-dibromo-4-hydroxybutyronitrile:

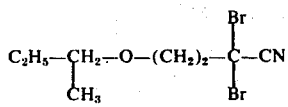

The conditions for this reaction, done in the presence of a reducing agent such as hexamethylphosphorous triamide, are essentially the same as for step *a* of Chart A.

In step *s*, cyanoepoxide XIX is hydrolyzed to replace $R_{21}$ with hydrogen, using conditions suitable for hydrolysis of esters or ethers. See, for example, step *d* and step *p*, above, as to deblocking. The alcohol moiety thus formed is then oxidized to an aldehyde moiety by methods known in the art, for example with Collins reagent (Tetrahedron Lett. 33663 (1968)).

In step *t*, the aldehyde compound XX is alkylated with an ylid by the Wittig reaction. The ylid is preferably formed from propyltriphenylphosphonium bromide and butyllithium using methods known in the art.

In step *u*, cyanoepoxide XXI is solvolyzed in formic acid. See step *b* of Chart A above.

In step *v*, monoformate XXII is converted to ketone XI either by first dehydrocyanating and then hydrolyzing the monoformate or by the reverse order. See steps *c–d* and *e–f* of Chart A discussed above.

Referring to Chart D, there are shown the steps by which cyanohydrin XVII (of Chart B) is transformed to ketone XXIII. Ketone XXIII is a useful intermediate in preparing 16-phenoxy-PGF$_{2\alpha}$ -type analogs.

In step w two successive reactions are carried out: deprotonating and reacting the carbanion thus produced with an aldehyde of the formula R$_{23}$CHO wherein R$_{23}$ is hydrogen or alkyl of 1 to 4 carbon atoms, inclusive. The conditions for deprotonating are those used above in step p of Chart B. The reaction with the aldehyde is done under anhydrous conditions, generally in an inert solvent such as tetrahydrofuran at about 25° C.

In step x, alkoxide anion XXIV of step w is arylated, for example by reaction with diphenyliodonium bromide or other suitable substituted phenyliodonium halide to provide the terminal group:

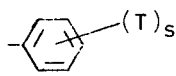

wherein T and s are as defined above. See for example Fieser et al., Reagents for Organic Synthesis, Vol. 1, p. 340, Wiley, New York, (1967).

In step y, cyanohydrin diether XXV is deblocked to replace R$_{16}$ groups with hydrogen, preferably using mildly acidic conditions. See step p of Chart B.

Finally, in step z the cyanohydrin XXVI is converted by dehydrocyanation to ketone XXIII. See step q of Chart B. Those formula-XXIII ketones wherein R$_{23}$ is not hydrogen exist as two epimers, both having the same configuration at the other asymmetric centers. These are separable by methods commonly applied to diastereomers, for example silica gel chromatography.

In the processes of Charts B, C, and D, as for Chart A, the products XI and XXIII are optically active if derived from optically active aldehyde VI, and racemic if derived from racemic aldehyde VI.

For convenience herein, names of racemic intermediates or products include the prefix "racemic" ("rac" or "dl"); when that prefix is absent, the intent is to designate an optically active compound.

DESCRIPTION OF THE PREFERRED EMBODIMENTS

The invention can be more fully understood by the following examples.

All temperatures are in degrees centigrade.

Infrared absorption spectra are recorded on a Perkin-Elmer Model 257 infrared spectrophotometer. Except when specified otherwise, chloroform solutions are used.

NMR spectra are recorded on a Varian A-60, A-60D, or T-60 spectrophotometer using deuterochloroform solutions with tetramethylsilane as an internal standard (downfield).

Mass spectra are recorded on a Varian Model MAT CH7 mass spectrometer or an LKB Model 9000 Gas Chromatograph-Mass Spectrometer (ionization voltage 70 ev).

"Brine", herein, refers to an aqueous saturated sodium chloride solution.

Silica gel chromatography, as used herein, is understood to include elution, collection of fractions, and combination of those fractions shown by TLC (thin layer chromatography) to contain the desired product free of starting material and impurities.

Skellysolve B consists of mixed isomeric hexanes.

EXAMPLE 1

2,2-Dibromoheptanenitrile

Bromine (14 ml.) is added to heptanenitrile, CH$_3$(CH$_2$)$_5$CN (26.64 g.) at 16°–38° C., followed by phosphorus tribromide (3.75 ml.) added in 4 portions. The mixture is heated at 60°–80° C. for 45 min. Additional bromine (24 ml.) is added within 10 min. The heating bath temperature is raised so that the reaction temperature is 88° C. for about 30 min. The mixture is cooled and shaken with a mixture of cold 9% sodium sulfite solution and Skellysolve B. The organic phase is washed with 20% aqueous sulfate, dried over sodium sulfate, and concentrated. Distillation yields the title compound, 36.47 g., b.p. 52°–57° C.

EXAMPLE 2

Tricyclic Lactone Cyanoepoxide (Formula VII wherein R$_{12}$ is n-pentyl and ~ is endo).

Refer to Chart A, step a. The formula-VII tricyclic lactone cyanoepoxide, namely 6-endo-(3-cyano-3-pentyl-2-oxiranyl)-3-exo-hydroxybicyclo[3.1.0]hexane-2-exo-acetic acid, γ-lactone, is prepared as follows. A mixture of the formula-VI endo tricyclic lactone aldehyde (U.S. Pat. No. 3,816,462, 4.0 g.), 2,2-dibromoheptanenitrile (Example 1, 7.75 g.), and 35 ml. of tetrahydrofuran is cooled to −15° C. and treated with hexamethylphosphorous triamide (5.26 ml.) in portions of about 0.5 ml. every 5 min., with the reaction temperature at −8° to −14° C. The mixture is stirred 2 hr. at a temperature of 31 10° to 0° C. The mixture is then shaken with 180 ml. of toluene and 30 ml. of brine. The organic phase is concentrated under reduced pressure to the formula-VII title compound, an oil, 8.54 g., having R$_f$ 0.42 (TLC on silica gel in ethyl acetate-benzene (1:4)); mass spectral peaks at 275, 246, and 217; infrared absorption at 2960, 2935, 2862, 2253, 1770, 1460, and 1190 cm$^{-1}$; and NMR peaks at 4.9, 3.2–2.5, 2.3, 2.0–1.2, and 1.0 δ.

EXAMPLE 3

Bicyclic Lactone Cyanohydrin Monoformate (Formula VIII wherein R$_{12}$ is n-pentyl).

Refer to Chart A, step b. The fomula-VIII bicyclic cyanohydrin monoformate, namely 2β-(3-cyano-3-hydroxy-1-octenyl)-3α-(formyloxy)-5α-hydroxy-1α-cyclopentaneacetic acid, γ-lactone, is prepared as follows. A solution of the formula-VII cyanoepoxide (Example 2, 148 mg.) in 0.2 ml. of dichloromethane is added to a mixture of anhydrous formic acid (0.95 ml.) and acetic anhydride (0.05 ml.) previously stirred for 0.5 hr. The reaction mixture is then stirred at about 25° C. for 1 hr. whereupon water (2.0 ml.) sodium carbonate (0.685 g.) and ethyl acetate (15 ml.) are added. The upper organic phase is washed with 1N, sodium bicarbonate (4.0 ml.) and both aqueous layers are washed with additional ethyl acetate (10 ml.). The combined organic extracts are dried and concentrated to yield the formula-VIII title compound in about 80% purity, 150 mg. Further purification by silica gel chromatography, eluting with ethyl acetate-benzene (1:4), yields the title compound, 75 mg., having infrared absorption at 3580–3210, 3013, 2960, 2941, 2872, 2263, 1771, 1724, 1182, and 925 cm$^{-1}$ and NMR peaks at 8.00, 5.45–5.42, 5.25–4.90, 2.46–2.40, 2.40–1.08, and 0.91 δ.

EXAMPLE 4

Bicyclic Lactone Monoformate (Formula IX wherein $R_{12}$ is n-pentyl).

Refer to Chart A, step c. The formula-IX bicyclic lactone monoformate, namely 3α-(formyloxy)-5α-hydroxy-2β-(3-oxo-trans-1-octenyl)-1α-cyclopentaneacetic acid, γ-lactone, is prepared as follows.

A mixture of the formula-VIII bicyclic lactone cyanohydrin monoformate (Example 3, 200 mg.) in tetrahydrofuran (4.0 ml.) is treated with 200 mg. of potassium carbonate and stirred at about 25° C. for 3.5 hr. The mixture is diluted with benzene (7 ml.), filtered, and concentrated to yield the formula-IX title compound, an oil, 190 mg., having infrared absorption at 2987, 2937, 1773, 1725, 1671, 1630, 1240, and 1178 cm$^{-1}$; and NMR peaks at 8.0, 6.6, 6.3, 5.1, 4.7–3.5, 3.5–1.9, and 3.6 δ.

The formula-IX bicyclic lactone monoformate of Example 4 is converted to PGF$_{2\alpha}$ by (a) reducing with excess zinc borohydride in dimethoxyethane at about 20° C. for 0.5 hr., (b) separating the 3-hydroxy epimers thereby formed, using silica gel chromatography, (c) deformylating by contacting the appropriate 3α-hydroxy epimer with water and p-toluenesulfonic acid in tetrahydrofuran at about 25°–40° C. to yield the corresponding bicyclic lactone diol, and (d) transforming the diol to PGF$_2$ by methods known in the art. See E. J. Corey et al., J. Am. Chem. Soc. 92, 397 (1970).

EXAMPLE 5

Bicyclic Lactone Ketone (Formula V wherein $R_{12}$ is n-pentyl).

Refer to Chart A, step d. The formula-V bicyclic lactone ketone, namely 3α,5α-dihydroxy-2β-(3-oxo-trans-1-octenyl)-1α-cyclopentaneacetic acid, γ-lactone, is prepared as follows. A mixture of the formula-IX bicyclic lactone monoformate (Example 4, 0.10 g.), 1 ml. of tetrahydrofuran, 0.05 ml. of water, and p-toluenesulfonic acid monohydrate (0.010 g.) is stirred at about 25° C. for 17 hr. Then 0.05 ml. of water is added and stirring is continued at 40° C. fo 7 hr. The mixture is diluted with benzene and washed with dilute aqueous sodium bicarbonate. The organic phase is dried and concentrated to yield the title compound, 0.08 g., having $R_f$ 0.27 (TLC on silica gel in ethyl acetatebenzene (1:1)); infrared absorption at 3605–3250, 3030, 3000, 2962, 2938, 2852, 1768, 1691, 1626, 1180, 1092, and 993 cm$^{-1}$; mass spectral peaks (TMS derivative) at 338, 323, 295, 281, 267, 248, 239, 221, 166, 145, 99, and 73; and NMR peaks at 6.99. 6.17, 4.95, 4.14, 3.25–2.9, 2.83–1.85, 1.76–1.07, and 0.88 δ.

The formula-V bicyclic lactone ketone of Example 5 is converted to PGF$_{2\alpha}$ by (a) benzoylating with benzoyl chloride in pyridine at about 20°–40° C. thereby forming 3α-benzoxy-5α-hydroxy-2β-(3-oxo-trans-1-octenyl)-1α-cyclopentaneactic acid, γ-lactone, (b) forming the corresponding bicyclic lactone diol, and (c) transforming the diol to PGF$_{2\alpha}$. See U.S. Pat. No. 3,778,450.

EXAMPLE 6

Bicyclic Lactone Cyanohydrin (Formula X wherein $R_{12}$ is n-pentyl).

Refer to Chart A, step e. The formula-X bicyclic lactone cyanohydrin, namely 2α-(3-cyano-3-hydroxy-1-octenyl)-3α,5α-dihydroxy-1α-cyclopentaneacetic acid, γ-lactone, is prepared as follows. The formula-VIII bicyclic lactone cyanohydrin monoformate (Example 3, 150 mg.) is dissolved in acetone (2 ml.), water (0.05 ml.) and p-toluenesulfonic acid (1 mg.), and the mixture is stirred at about 25° C. for 19 hr. Thereafter the mixture is extracted with ethyl acetate, dried, and concentrated to yield the formula-X title compound an oil, 120 mg., having mass spectral peaks (TMS derivative) at 437, 442, 410, 367, 239, and 197; infrared absorption at 3600–3150, 3012, 2960, 2941, 2872, 1769, 1460, 1180, 984, and 922 cm$^{-1}$; and NMR peaks at 5.78, 4.95, 3.90–4.45, 2.51–2.70, 1.14–2.35, and 0.91 δ.

EXAMPLE 7

Bicyclic Lactone Ketone (Formula V wherein $R_{12}$ is n-pentyl).

Refer to Chart A, steps b, c, and d. The formula-V bicyclic lactone ketone, namely 3α,5α-dihydroxy-2β-(3-oxo-trans-1-octenyl)-1α-cyclopentaneacetic acid, γ-lactone, is prepared as follows.

I. The formula-VIII bicyclic lactone cyanohydrin monoformate wherein $R_{12}$ is n-pentyl is first prepared. A solution of the formula-VII cyanoepoxide (EXample 2, 8.54 g.) in 7 ml. dichloromethane is added to a mixture of anhydrous formic acid (44.4 ml.) and acetic anhydride (1.16 ml.) previously stirred for 0.5 hr. The reaction mixture is then stirred at about 25° C. for 23 hr., concentrated, and the resulting cyanohydrin monoformate used directly.

II. The product of part I is taken up in tetrahydrofuran (72 ml.) and treated with 24 ml. of 10% sulfuric acid, with stirring continued at about 25° C. for 21 hr. Thereafter sodium carbonate (2.18 g.) is added and the tetrahydrofuran removed under reduced pressure. The residue is extracted with ethyl acetate and the resulting ethyl acetate solution is backwashed with water (60 ml.) and then 1N. sodium bicarbonate solution. The aqueous phases are backwashed with ethyl acetate and all of the ethyl acetate extracts are combined, stirred with 1N. sodium bicarbonate solution and separated. The upper (organic) layer is washed with brine, dried over sodium sulfate, and concentrated to yield the formula-V title compound, 7.19 g. in about 65% purity.

The formula-V product is further purified either by silica gel chromatography, or, preferably, by liquid-liquid extraction followed by crystallization, as follows.

III. A solution of the formula-V ketone of part I (6.998 g.) in 19 ml. of ethyl acetate is subjected to a multi-stage liquid-liquid extraction. Each stage contains a lower phase (412 ml.) and an upper phase (206 ml.) from equilibrated acetone-Skellysolve B (isomeric hexanes)-water (1:1:1).

The impurities are concentrated in the upper phase. The product is obtained by concentrating the lower phase and extracting with ethyl acetate (washing each extract with brine). The ethyl acetate solution is dried over sodium sulfate and concentrated to yield the formula-V title compound, 5.707 g. in about 80% purity.

IV. Further purification is achieved by crystallization as follows. A solution of the formula-V compound from part III (5.626 g.) in tetrahydrofuran (4.0 ml.) and isopropyl ether (15 ml.) is cooled to −15° C. and seeded. Additional isopropyl ether (25 ml.) is added slowly while cooling at −25° C. The resulting solid is washed with cold isopropyl ether (5 ml.) and dried The rsulting semisolid product (4.688 g.) is recrystallized from tetrahydrofuran (2.4 ml.) and isopropyl ether (5.0 ml.) as above to yield the formula-V title compound, 4.1147 g. Additional product is obtained from the mother liquors by silica gel chromatography, eluting with ethyl acetate-benzene (1:4) 0.514 g.

EXAMPLE 8

Bicyclic Lactone Ketone (Formula V wherein $R_{12}$ is n-pentyl).

Refer to Chart A, step f. The formula-V bicyclic lactone ketone, namely 3α,5α-dihydroxy-2β-(3-oxo-trans-1-octenyl)-1α-cyclopentane-acetic acid, γ-lactone, is prepared as follows. A mixture of the formula-X bicyclic lactone cyanohydrin (Example 6, 4.35 g.) in 45 ml. of tetrahydrofuran and 45 ml. of benzene, with potassium carbonate (4.5 g.), is stirred at about 25° C. for 21 hr. The mixture is diluted with benzene (100 ml.), filtered, and concentrated to an oil, 3.618 g. The oil is subjected to silica gel chromatography, eluting with ethyl acetatebenzene (1:4), and concentrating to yield the formula-V title compound, an oil, 1.4753 g., having the same properties as reported above in Example 5.

Following the procedures of Examples 1–8 but replacing heptanenitrile with 3,3-dimethylheptanenitrile, there is first obtained 2,2-dibromo-3,3-dimethylheptanenitrile which is further reacted as in Example 2 to yield the formula-VII 6-endo-[3-cyano-3-(1,1-dimethylpentyl)-2-oxiranyl]-3-exo-hydroxybicyclo-[3.1.0]hexane-2-exo-acetic acid, γ-lactone; there is finally obtained the corresponding formula-V bicyclic lactone ketone wherein $R_{12}$ is

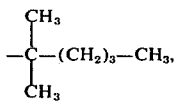

namely 3α,5α-dihydroxy-2β-(4,4-dimethyl-3-oxo-trans-1-octenyl)-1α-cyclopentaneacetic acid, γ-lactone. That ketone is useful in preparing 16,16-dimethyl-PGF$_2$ by methods known in the art.

Likewise following the procedures of Examples 1–8 but replacing heptanenitrile with 3,3-difluoroheptanenitrile, there is finally obtained the corresponding formula-V bicyclic lactone ketone wherein $R_{12}$ is —CF$_2$—(CH$_2$)$_3$—CH$_3$, namely 3α,5α-dihydroxy-2β-(4,4-difluoro-3-oxo-trans-1-octenyl)-1α-cyclopentaneacetic acid, γ-lactone, useful for preparing 16,16-difluoro-PGF$_2$ by methods known in the art.

Following the procedures of Example 2–8 but replacing 2,2-dibromoheptanenitrile with 2,2-dibromo-4-phenylbutyronitrile, there is obtained the corresponding formula-V bicyclic lactone ketone wherein $R_{12}$ is

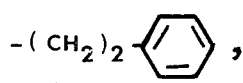

namely 3α,5α-dihydroxy-2β-(3-oxo-5-phenyl-trans-1-pentyl)1α-cyclopentaneacetic acid, γ-lactone, useful for preparing 17-phenyl-18,19,20-trinor-PGF$_{2\alpha}$ by methods known in the art.

Likewise following the procedures of Examples 2–8 but replacing 2,2-dibromoheptanenitrile with each of the following dihalonitriles:

a. 2,2-dibromohexanenitrile
b. 2,2-dichlorooctanenitrile
c. 2,2-diiodo-3-methylhexanenitrile
d. 2,2-diiodo-3-fluorooctanenitrile
e. 2,2-dibromo-cis-4-heptenenitrile
f. 2,2-dibromo-3-phenylpropionitrile
g. 2,2-dichloro-4-(4-chlorophenyl)butyronitrile
h. 2,2-dibromo-4-[(3-trifluoromethyl)phenyl]-butyronitrile
i. 2,2-diiodo-4-(2-fluorophenyl)butyronitrile
j. 2,2-dibromo-4-(4-methoxyphenyl)butyronitrile
k. 2,2-dibromo-3-phenoxypropionitrile, there are obtained the corresponding formula-V bicyclic lactone ketones wherein $R_{12}$ is, respectively:

a. —(CH$_2$)$_3$—CH$_3$
b. —(CH$_2$)$_5$—CH$_3$
c. —CH(CH$_3$)—(CH$_2$)$_2$—CH$_3$
d. —CHF—(CH$_2$)$_4$—CH$_3$
e. 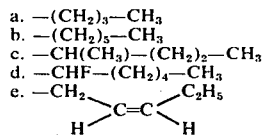

(f) 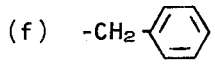

(g) 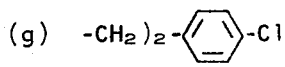

(h) 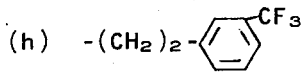

(i) 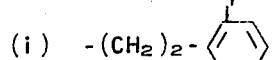

(j) 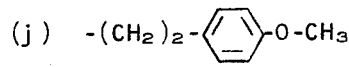

(k) 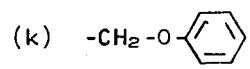

Following the procedures of Examples 2–8 and of the paragraphs following Example 8 but replacing the endo form of the formula-VI aldehyde with the exo form, the corresponding formula-VII exo tricyclic lactone cyanoepoxides are obtained which are finally converted to the formula-V bicyclic lactone ketones.

Also following the procedures of Examples 2–8 and of the paragraphs following Example 8, but replacing the optically active formula-VI aldehyde with the racemic mixture of either the endo or exo form, there are obtained the racemic mixtures corresponding to the compounds of formulas V, VII, VIII, IX, and X.

EXAMPLE 9

Tricyclic Lactone Cyanoepoxide (Formula XII wherein ~ is endo).

Refer to Chart B. The formula-XII tricyclic lactone cyanoepoxide, namely 6-endo-(3-carbethoxy-3-cyano-2-oxiranyl)-3-exo-hydroxybicyclo[3.1.0]hexane-2-exo-acetic acid, γ-lactone, is prepared as follows. A mixture of the formula-VI (Chart A) endo tricyclic lactone aldehyde (U.S. Pat. No. 3,816,462, 166 g.), the ethyl ester of dibromocyanoacetic acid (2.98 g.), and 35 ml. of tetrahydrofuran previously cooled to −10° C. is treated dropwise with hexamethylphosphorous triamide (1.79 g.) added dropwise. After complete reaction, as shown by TLC, the mixture is worked up to yield the title compound, as isomeric epoxides.

EXAMPLE 10

Bicyclic Lactone Carbethoxy Cyanohydrin (Formula XIV).

Refer to Chart B, step $j$. The formula-XIV bicyclic lactone carbethoxy cyanohydrin, namely 2$\beta$-(3-carbethoxy-3-cyano-3-hydroxy-1-propenyl)-3$\alpha$,5$\alpha$-dihydroxy-1$\alpha$-cyclopentaneacetic acid, $\gamma$-lactone, is prepared as follows. The formula-XII tricyclic lactone cyanoepoxide (Example 9) is dissolved in a minimum volume of dichloromethane and, using a mixture of anhydrous formic acid and acetic anhydride following the procedure of Example 3, transformed to the 3-monoformate of the title compound. After replacement of formyl with hydroxyl by hydrolysis with dilute sulfuric acid in tetrahydrofuran solution and work-up as in Example 6, the title compound is obtained.

EXAMPLE 11

Bicyclic Lactone Cyanohydrin (Formula XV).

Refer to Chart B, step $k$. The formula-XV bicyclic lactone cyanohydrin, namely 2$\beta$-(3-cyano-3-hydroxy-1-propenyl)-3$\alpha$,5$\alpha$-dihydroxy-1$\alpha$-cyclopentaneacetic acid, $\gamma$-lactone, is prepared as follows. The formula-XIV bicyclic lactone carbethoxy cyanohydrin (Example 10) is hydrolyzed under vigorous conditions in dilute sulfuric acid and tetrahydrofuran so that ester cleavage and decarboxylation occur to yield the title compound.

EXAMPLE 12

Bicyclic Lactone Cyanohydrin Diether (Formula XVII wherein $R_{16}$ is 1-ethoxyethyl).

Refer to Chart B. The formula-XVII bicyclic lactone cyanohydrin diether namely 2$\beta$-[3-cyano-3-(1-ethoxyethoxy)-1-propenyl]-3$\alpha$-(1-ethoxyethyl)-5$\alpha$-hydroxy-1$\alpha$-cyclopentaneacetic acid, $\gamma$-lactone, is prepared as follows.

I. Refer to step $l$. The formula-XV bicyclic lactone cyanohydrin (Example 11, 2.2 g.) in 72 ml. of toluene is cooled to −10° C. and treated with 9.6 ml. of ethyl vinyl ether and p-toluenesulfonic acid (5 mg.). After the reaction is complete, after about 18 hr. at −10° to 0° C., excess reagent is removed under reduced pressure and the catalyst is neutralized with triethylamine. The mixture is concentrated to yield the title compound.

II. Refer to step $m$. Alternately, there is first prepared the formula-XVI bicyclic lactone carbethoxy cyanohydrin diether, namely 2$\beta$-[3-carbethoxy 3-cyano-(1-3-ethoxyethoxy)-1-propenyl]-3$\alpha$-(1-ethoxyethoxy)-5$\alpha$-hydroxy-1$\alpha$-cyclopentaneacetic acid, $\gamma$-lactone as follows. The formula-XIV bicyclic lactone carbethoxy cyanohydrin (Example 10) is treated with ethyl vinyl ether, following the procedure in part I above.

III. Refer to step $n$. Next, the title compound is prepared by decarboxylation as follows. The formula-XVI diether of Part II above (1.0 g.) is treated in dimethyl sulfoxide (10 ml.) with sodium cyanide (0.2 g.) and heated to 160° C. The reaction mixture is diluted with 30 ml. of water and extracted with benzene. The organic extract is backwashed with brine, dried, and concentrated under reduced pressure to yield the title compound.

EXAMPLE 13

Bicyclic Lactone Cyanohydrin (Formula XVIII).

Refer to Chart B, step $p$. The formula-XVII bicyclic lactone cyanohydrin, namely 2$\beta$-(3-cyano-3-hydroxy-trans-1,cis-5-octadienyl)-3$\alpha$,5$\alpha$-dihydroxy-1$\alpha$-cyclopentaneacetic acid, $\gamma$-lactone is prepared as follows.

I. Deprotonation.

The formula-XVII bicyclic lactone cyanohydrin diether (Example 12, 3.67 g.) in tetrahydrofuran is treated at about −78° C. with lithium diisopropylamide (10 mmole) and the mixture warmed to −40° C.

II. Alkylation and Deblocking.

The anion of part I above in tetrahydrofuran solution is treated with 1-bromo-cis-2-pentene (1.48 g.). After reaction is complete as shown by TLC, aqueous citric acid is added to pH 2.0 and the mixture is stirred at 30° C. for about 4 hr. to effect deblocking (replacement of 1-ethoxyethoxy groups with hydroxy). The mixture is concentrated under reduced pressure to remove tetrahydrofuran. Ethyl acetate (10 ml.) is added, the phases are separated, and the queous layer again extracted with ethyl acetate. The combined organic extracts are concentrated under reduced pressure to yield the title compound.

EXAMPLE 14

Bicyclic Lactone Ketone (Formula XI).

Refer to Chart B, step $q$. The formula-XI bicyclic lactone ketone, namely 3$\alpha$,5$\alpha$-dihydroxy-2$\beta$-(3-oxo-trans-1,cis-5-octadienyl)-1$\alpha$-cyclopentaneactic acid, $\gamma$-lactone, is prepared as follows. The formula-XVIII bicyclic lactone cyanohydrin (Example 13) in ethyl acetate is stirred with 1N. sodium bicarbonate (10 ml.) at about 25° C. for 4 hr. to effect dehydrocyanation. The organic phase is separated, dried over sodium sulfate, and concentrated to obtain the title compound.

EXAMPLE 15

Bicyclic Lactone Ketone (Formula XI)

Refer to Chart C. The formula-XI bicyclic lactone ketone, namely 3$\alpha$,5$\alpha$-dihydroxy-2$\beta$-(3-oxo-trans-1,cis-5-octadienyl)-1$\alpha$-cyclopentaneacetic acid, $\gamma$-lactone, is prepared as follows.

I. Refer to step $r$. A mixture of the formula-VI endo tricyclic lactone aldehyde (4.0 g.), the 2,2-dibromo-4-hydroxybutyronitrile ester of acetic acid (8.2 g.), and 35 ml. of tetrahydrofuran is cooled to −15° C. and treated with hexamethylphosphorous triamide (5.26 ml.) in portions at about −10° C., continuing stirring for an additional 2 hr. at 10° C. The mixture is worked up to yield the formulation XIX cyanoepoxide.

II. Refer to step $s$. The product of part I is hydrolyzed in dilute sulfuric acid to replace the acetyl group ($R_{21}$) with hydrogen. Thereafter, using Collins reagent (Tetr. Lett. 3363 (1968)) in dichloromethane at about 0° C., the formula-XX aldehyde is obtained.

III. Refer to step $t$. The product of part II is subjected to Wittig alkylation, adding it to a suspension of propyltriphenylphosphonium bromide in benzene containing the equivalent amount of n-butyllithium. The mixture is finally heated at about 50°–70° C. for 2.5 hr. The mixture is cooled and filtered, and the solids washed with benzene. The combined filtrate and washes are concentrated somewhat, then washed with dilute hydrochloric acid and water. The organic phase is dried and concentrated to yield the formula-XXI cyanoepoxide.

IV. Refer to step $u$. The product of part III is added to a mixture of anhydrous formic acid (2.0 ml.) and acetic anhydride (0.1 ml.) previously stirred for 0.5 hr. The mixture is then stirred at about 25°C. for one hr. and quenched with aqueous sodium carbonate. The product is extracted ito ethyl acetate and worked up to yield the formula-XXII cyanohydrin monoformate.

V. Refer to step $v$. Thereafter, the product of part IV is first hydrolyzed in tetrahydrofuran with 10% sulfuric acid at about 40° C. The solvent is removed and the residue extracted with ethyl acetate. The formyl-free cynohydrin obtained by concentration is then contacted with potassium carbonate in tetrahydrofuran and benzene at about 25° C. for 21 hr. to produce the formula-XI ketone.

EXAMPLE 16

Bicyclic Lactone Ketone (Formula XXIII wherein $R_{23}$ is hydrogen and $s$ is zero).

Refer to Chart D. The formula-XXIII bicyclic lactone ketone, namely 3α,5α-dihydroxy-2β-(3-oxo-4-phenoxy-trans-1-butenyl)-1α-cyclopentaneacetic acid, γ-lactone is prepared as follows.

I. Refer to step $w$. The formula-XVII bicyclic lactone cyanohydrin diether (Example 12, 3.67 g.) is deprotonated following the procedure of Example 13, part I. Then, to a solution of the anion in tetrahydrofuran is added gaseous formaldehyde formed by pyrolyzing paraformaldehyde. The resulting formula-XXIV alkoxide wherein $R_{23}$ is hydrogen and $s$ is zero is used directly without isolation.

II. Refer to step $x$. The reaction mixture of part I is arylated by treatment with diphenyliodonium bromide. See Fieser et al., Reagents for Organic Synthesis, Vol. 1, p. 340, Wiley, New York (1967). The formula-/XXV diether is isolated, either by extraction or chromatography.

III. Refer to step $y$. The formula-XXVI cyanohydrin is obtained by deblocking the product of part II. A mixture of the formula-XXV diether (0.5 g.) in tetrahydrofuran (10 ml. with aqueous citric acid (ca. 2N.) added to pH 2.0 is stirred at about 30° C. until the reaction is complete as shown by TLC. The tetrahydrofuran is removed under reduced pressure, and the remainder is extracted repeatedly with ethyl acetate. The combined extracts contain the formula-XXVI cyanohydrin wherein $R_{23}$ is hydrogen and $s$ is zero.

IV. Refer to step $z$. Finally, the title compound is obtained by dehydrocyanation of the product of part III in aqueous sodium bicarbonate (10 ml., 1N) for 4 hr. at about 25° C. The phases are separated and the organic phase is dried and concentrated under reduced pressure to yield the formula-XXIII bicyclic lactone ketone.

Following the procedures of Example 16 but replacing formaldehyde in step I with acetaldehyde, there is obtained the corresponding formula-XXIII bicyclic lactone ketone in which $R_{23}$ is methyl, namely 3α,5α-dihydroxy-2β-(3-oxo-4-methyl-4-phenoxy-trans-1-butenyl)-1α-cyclopentaneacetic acid, γ-lactone.

Likewise following the procedures of Example 16 but replacing the optically active formula-XVII starting material with the corresponding racemic mixture, there are obtained the racemic mixtures corresponding to the compounds of formulas XXIII, XXIV, XXV, and XXVI.

I claim:

1. A process for preparing an optically active bicyclic lactone ketone of the formula

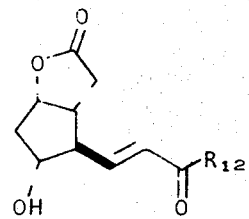

or a mixture of that compound and the enantiomer thereof, wherein $R_{12}$ is

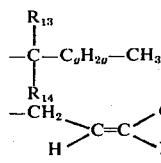

or

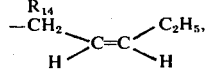

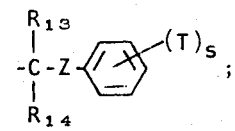

wherein $C_gH_{2g}$ is alkylene of one to 9 carbon atoms, inclusive, with 1 to 5 carbon atoms, inclusive, in the chain betweem $—CR_{13}R_{14}—$ and terminal methyl; wherein $R_{13}$ and $R_{14}$ are hydrogen, alkyl of 1 to 4 carbon atoms, inclusive, or fluoro, being the same or different, with the proviso that $R_{13}$ is fluoro only when $R_{14}$ is hydrogen or fluoro; wherein T is alkyl of 1 to 4 carbon atoms, inclusive, fluoro, chloro, trifluoromethyl, or $—OR_{15}$, wherein $R_{15}$ is hydrogen or alkyl of 1 to 4 carbon atoms. inclusive, and $s$ is zero, 1, 2, or 3, with the proviso that no more than two T's are other than alkyl; and wherein Z represents an oxa atom (—O—) or $C_jH_{2j}$, wherein $C_jH_{2j}$ is a valence bond or alkylene of 1 to 9 carbon atoms, inclusive, substituted with zero, 1, or 2 fluoro, with 1 to 6 carbon atoms, inclusive, between $—CR_{13}R_{14}—$ and the ring; which comprises a. starting with a tricyclic lactone aldehyde of the formula

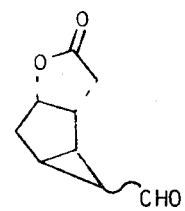

or a mixture of that compound and the enantiomer thereof, wherein ~ indicates attachment to the cyclopropane ring in endo or exo configuration, and reacting said aldehyde with a nitrile of the formula

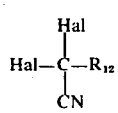

wherein Hal is chloro, bromo, or iodo, the two Hal's being the same or different, and wherein R₁₂ is defined as above, to form an optically active cyanoepoxide of the formula

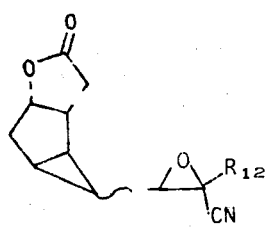

or a mixture of that compound and the enantiomer thereof, wherein R₁₂ and ~ are as defined above;

b. reacting said cyanoepoxide with formic acid to produce an optically active cyanohydrin monoformate of the formula

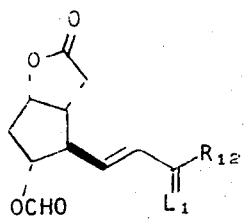

or a mixture of that compound and the enantiomer thereof, wherein R₁₂ is as defined above and wherein L₁ represents

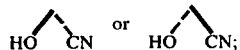

and c. transforming the product of step (b) to said bicyclic lactone ketone by d. removing hydrocyanic acid by dehydrocyanation to convert the

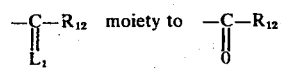

and e. replacing formyl with hydroxyl, said steps (d) and (e) being performed either in the order (d)–(e) or (e)–(d).

2. A process according to claim 1 wherein R₁₂ is

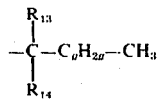

wherein $C_aH_{2a}$ is alkylene of one to 9 carbon atoms, inclusive, with one to 5 carbon atoms, inclusive, in the chain between —CR₁₃R₁₄— and terminal methyl; wherein R₁₃ and R₁₄ are hydrogen, alkyl of one to 4 carbon atoms, inclusive, or fluoro, being the same or different, with the proviso that R₁₃ is fluoro only when R₁₄ is hydrogen or fluoro.

3. A process according to claim 1 wherein R₁₂ is

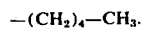

4. A process according to claim 1 wherein R₁₂ is

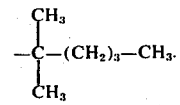

5. A process according to claim 1 wherein R₁₂ is

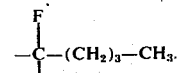

6. A process according to claim 1 wherein R₁₂ is

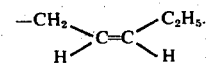

7. A process according to claim 1 wherein R₁₂ is

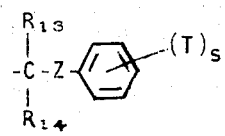

wherein R₁₃ and R₁₄ are hydrogen, alkyl of one to 4 carbon atoms, inclusive, or fluoro, being the same or different, with the proviso that R₁₃ is fluoro only when R₁₄ is hydrogen or fluoro; wherein T is alkyl of 1 to 4 carbon atoms, inclusive, fluoro, chloro, trifluoromethyl, or —OR₁₅, wherein R₁₅ is hydrogen or alkyl of 1 to 4 carbon atoms, inclusive, and s is zero, 1, 2, or 3, with the proviso that not more than two T's are other than alkyl; and wherein Z represents an oxa atom (—O—) or $C_jH_{2j}$, wherein $C_jH_{2j}$ is a valence bond or alkylene of 1 to 9 carbon atoms, inclusive, substituted with zero, 1, or 2 fluoro, with 1 to 6 carbon atoms, inclusive, between —CR₁₃R₁₄— and the ring.

8. A process according to claim 7 wherein Z is an oxa atom.

9. A process according to claim 7 wherein Z is methylene.

10. A process for preparing an optically active bicyclic lactone cyanohydrin monoformate of the formula

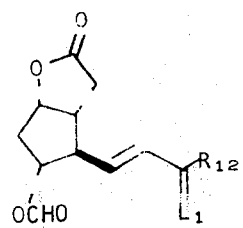

or a mixture of that compound and the enantiomer thereof, wherein $R_{12}$ is

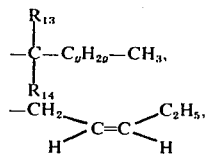 (1)

(2)

or (3) 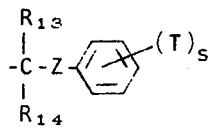

wherein $C_gH_{2g}$ is alkylene of 1 to 9 carbon atoms, inclusive, with 1 to 5 carbon atoms, inclusive, in the chain between —$CR_{13}R_{14}$— and terminal methyl; wherein $R_{13}$ and $R_{14}$ are hydrogen, alkyl of 1 to 4 carbon atoms, inclusive, or fluoro, being the same or different, with the proviso that $R_{13}$ is fluoro only when $R_{14}$ is hydrogen or fluoro; wherein T is alkyl of 1 to 4 carbon atoms, inclusive, fluoro, chloro, trifluoromethyl, or —$OR_{15}$, wherein $R_{15}$ is hydrogen or alkyl of 1 to 4 carbon atoms, inclusive, and $s$ is zero, 1, 2, or 3, with the proviso that not more than two T's are other than alkyl; wherein Z represents an oxa atom (—O—) or $C_jH_{2j}$, wherein $C_jH_{2j}$ is a valence bond or alkylene of 1 to 9 carbon atoms, inclusive, substituted with zero, one, or 2 fluoro, with 1 to 6 carbon atoms, inclusive, between —$CR_{13}R_{14}$—and the ring; and wherein $L_1$ represents

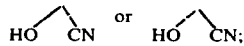

which comprises a. starting with a tricyclic lactone aldehyde of the formula

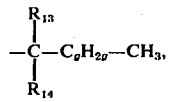

or a mixture of that compound and the enantiomer thereof, wherein ~ indicates attachment to the cyclopropane ring in endo or exo configuration, and reacting said aldehyde with a nitrile of the formula

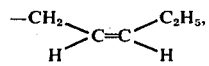

wherein Hal is chloro, bromo, or iodo, the two T's being the same or different, and wherein $R_{12}$ is defined as above, to form an optically active cyanoepoxide of the formula

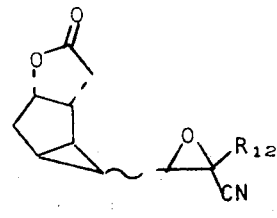

or a mixture of that compound and the enantiomer thereof, wherein $R_{12}$ and ~ are as defined above; and b. reacting said cyanoepoxide with formic acid.

11. A process for preparing an optically active tricyclic lactone cyanoepoxide of the formula or a mixture of that compound and the enantiomer thereof, wherein $R_{12}$ is (1)

(2)

or (3)

wherein $C_gH_{2g}$ is alkylene of 1 to 9 carbon atoms, inclusive, with 1 to 5 carbon atoms, inclusive, in the chain between —$CR_{13}R_{14}$— and terminal methyl; wherein $R_{13}$ and $R_{14}$ are hydrogen, alkyl of 1 to 4 carbon atoms, inclusive, or fluoro, being the same or different, with the proviso that $R_{13}$ is fluoro only when $R_{14}$ is hydrogen or fluoro; wherein T is alkyl of 1 to 4 carbon atoms, inclusive, fluoro, chloro, trifluoromethyl, or —$OR_{15}$, wherein $R_{15}$ is hydrogen or alkyl of 1 to 4 carbon atoms, inclusive, and $s$ is zero, 1, 2, or 3, with the proviso that not more than two T's are other than alkyl; and wherein Z represents an oxa atom (—O—) or $C_jH_{2j}$, wherein $C_jH_{2j}$ is a valence bond or alkylene of 1 to 9 carbon atoms, inclusive, substituted with zero, one, or 2 fluoro, with 1 to 6 carbon atoms, inclusive, between —$CR_{13}R_{14}$— and the ring; and wherein ~ indicates attachment to the cyclopropane ring in endo or exo configuration;

which comprises starting with a tricyclic lactone aldehyde of the formula

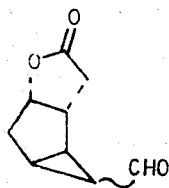

or a mixture of that compound and the enantiomer thereof, wherein ~ is as defined above, and reacting said aldehyde with a nitrile of the formula

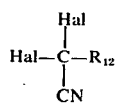

wherein Hal is chloro, bromo, or iodo, the two Hal's being the same or different, and wherein $R_{12}$ is defined as above.

12. A process according to claim 11 wherein $R_{12}$ is

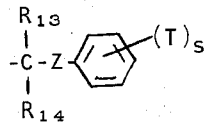

wherein $R_{13}$, $R_{14}$, $s$, T, and Z are as defined in claim 11.

13. A process according to claim 12 wherein $R_{13}$ and $R_{14}$ are hydrogen, $s$ is zero, and Z is an oxa atom (—O—).

14. A process for preparing an optically active bicyclic lactone ketone of the formula

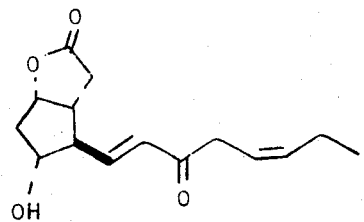

or a mixture of that compound and the enantiomer thereof, which comprises a. starting with a tricyclic lactone cyanoepoxide of the formula

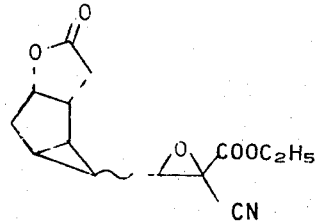

or a mixture of that compound and the enantiomer thereof, wherein ~ indicates attachment to the cyclopropane ring in endo or exo configuration, and reacting said cyanoepoxide with formic acid to produce an optically active cyanohydrin monoformate of the formula

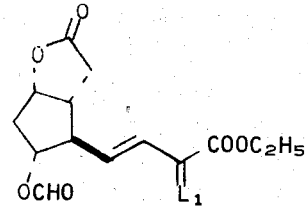

or a mixture of that compound and the enantiomer thereof, wherein $L_1$ represents

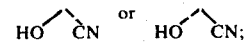

b. replacing formyl with hydroxyl to produce an optically active cyanohydrin of the formula

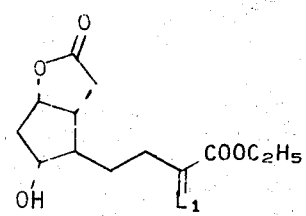

or a mixture of that compound and the enantiomer thereof, wherein $L_1$ is as defined above;

c. transforming the product of step (b) to form a diether of the formula

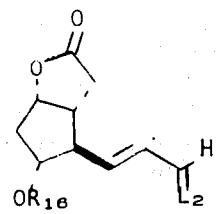

or a mixture of that compound and the enantiomer thereof, wherein $L_2$ represents

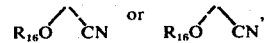

wherein $R_{16}$ is 1-ethoxyethyl, tetrahydropyranyl, tetrahydrofuranyl, or a group of the formula

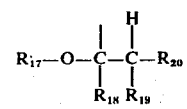

wherein $R_{17}$ is alkyl of one to 17 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of 1 to 4 carbon atoms, inclusive, wherein $R_{18}$ and $R_{19}$ are the same or different, being hydrogen, alkyl of one to 4 carbon atoms, inclusive, phenyl or phenyl substituted with one, 2, or 3 alkyl of 1 to 4 carbon atoms, inclusive, or, when $R_{18}$ and $R_{19}$ are taken together, $-(CH_2)_a-$ or $-(CH_2)_b-O-(CH_2)_c-$ wherein $a$ is 3, 4, or 5, $b$ is 1, 2, or 3, and $c$ is 1, 2, or 3 with the proviso that $b$ plus $c$ is 2, 3, or 4, and wherein $R_{20}$ is hydrogen or phenyl: by d. replacing the hydrogen of the hydroxyl groups with $R_{16}$ groups wherein $R_{16}$ is as defined above, and
e. replacing the $-COOC_2H_5$ moiety with hydrogen, said steps (d) and (e) being performed either in the order (d)-(e) or (e)-(d);
f. transforming the product of step (c) to a compound of the formula

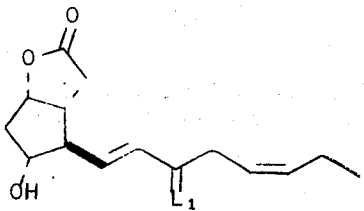

or a mixture of that compound and the enantiomer thereof, wherein ~ is as defined above by the steps of deprotonating, alkylating with 1-bromo-cis-2-pentene, and deblocking and g. removing hydrocyanic acid by dehydrocyanation to convert the

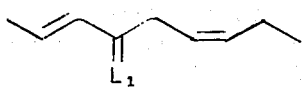 moiety to

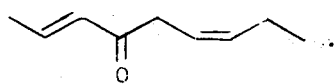

15. A process for preparing an optically active bicyclic lactone ketone of the formula

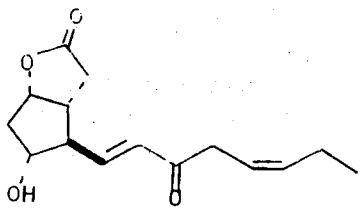

or a mixture of that compound and the enantiomer thereof, which comprises a. starting with a tricyclic lactone aldehyde of the formula

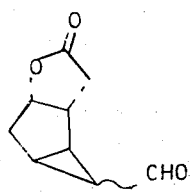

or a mixture of that compound and the enantiomer thereof, wherein ~ indicates attachment to the cyclopropane ring in endo or exo configuration, and reacting said aldehyde with a nitrile of the formula

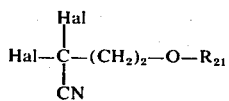

wherein Hal is chloro, bromo, or iodo, the two Hal's being the same or different, and wherein $R_{21}$ is (1) $R_{16}$, defined as 1-ethoxyethyl, tetrahydropyranyl, tetrahydrofuranyl, or a group of the formula

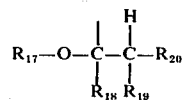

wherein $R_{17}$ is alkyl of one to 17 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{18}$ and $R_{19}$ are the same or different, being hydrogen, alkyl of 1 to 4 carbon atoms, inclusive, phenyl or phenyl substituted with one, 2, or 3 alkyl of 1 to 4 carbon atoms, inclusive, or, when $R_{18}$ and $R_{19}$ are taken together, $-(CH_2)_a-$ or $-(CH_2)_b-O-(CH_2)_c-$ wherein $a$ is 3, 4, or 5, $b$ is 1, 2, or 3, and $c$ is 1, 2, or 3 with the proviso that $b$ plus $c$ is 2, 3, or 4, and wherein $R_{20}$ is hydrogen or phenyl; or (2) carboxyacyl $-C(O)R_{22}$ wherein $R_{22}$ is hydrogen or alkyl of 1 to 17 carbon atoms, inclusive, to form an optically active cyanoepoxide of the formula

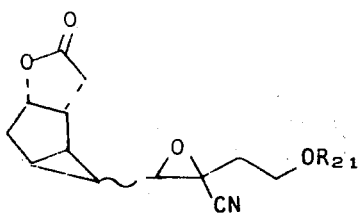

or a mixture of that compound and the enantiomer thereof, wherein $R_{21}$ and ~ are as defined above;

b. transforming the product of step (a) to a compound of the formula

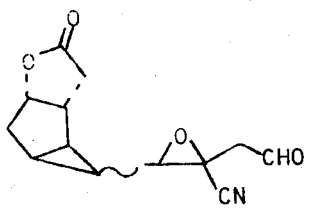

or a mixture of that compound and the enantiomer thereof, wherein ~ is as defined above, by hydrolyzing $-CH_2CH_2-O-R_{21}$ to $-CH_2CH_2-OH$ and thereafter oxidizing $-CH_2CH_2-OH$ to $-CH_2CHO$;

c. transforming the product of step (b) to a cyanoepoxide of the formula

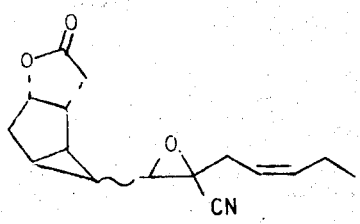

or a mixture of that compound and the enantiomer thereof, wherein ~ is as defined above;

d. reacting said cyanoepoxide with formic acid to produce an optically active cyanohydrin monoformate of the formula

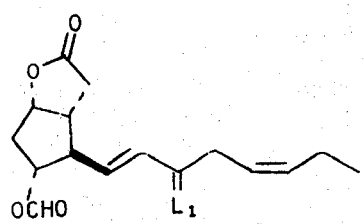

or a mixture of that compound and the enantiomer thereof, wherein $L_1$ represents

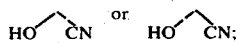

and e. transforming the product of step (d) to said bicyclic lactone ketone by f. removing hydrocyanic acid by dehydrocyanation to convert the

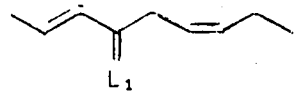 moiety to

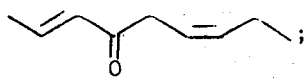;

and g. replacing formyl with hydroxyl, said steps (f) and (g) being performed either in the order (f)–(g) or (g)–(f).

16. An optically active compound of the formula

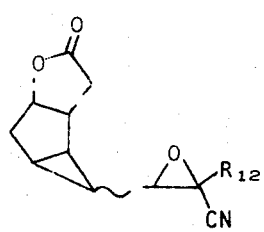

or a mixture of that compound and the enantiomer thereof, wherein $R_{12}$ is

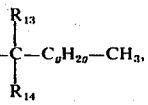 (1)

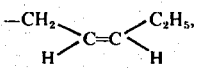 (2)

or (3) 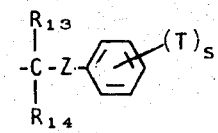

wherein $C_gH_{2g}$ is alkylene of 1 to 9 carbon atoms, inclusive, with 1 to 5 carbon atoms, inclusive, in the chain between —$CR_{13}R_{14}$— and terminal methyl; wherein $R_{13}$ and $R_{14}$ are hydrogen, alkyl of 1 to 4 carbon atoms, inclusive, or fluoro, being the same or different, with the proviso that $R_{13}$ is fluoro only when $R_{14}$ is hydrogen or fluoro; wherein T is alkyl of 1 to 4 carbon atoms, inclusive, fluoro, chloro, trifluoromethyl, or —$OR_{15}$, wherein $R_{15}$ is hydrogen or alkyl of 1 to 4 carbon atoms, inclusive, and $s$ is zero, 1, 2, or 3, with the proviso that not more than two T's are other than alkyl; and wherein Z represents an oxa atom (—O—) or $C_jH_{2j}$, wherein $C_jH_{2j}$ is a valence bond or alkylene of 1 to 9 carbon atoms, inclusive, substituted with zero, 1, or 2 fluoro, with 1 to 6 carbon atoms, inclusive, between —$CR_{13}R_{14}$— and the ring; and wherein ~ indicates attachment in endo or exo configuration.

17. An optically active compound according to claim 16.

18. A compound according to claim 17 wherein $R_{12}$ is

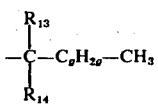

wherein $C_gH_{2g}$ is alkylene of 1 to 9 carbon atoms, inclusive, with 1 to 5 carbon atoms, inclusive, in the chain between —$CR_{13}R_{14}$— and terminal methyl; wherein $R_{13}$ and $R_{14}$ are hydrogen, alkyl of 1 to 4 carbon atoms, inclusive, or fluoro, being the same or different, with the proviso that $R_{13}$ is fluoro only when $R_{14}$ is hydrogen or fluoro.

19. A compound according to claim 17 wherein $R_{12}$ is —(CH$_2$)$_4$—CH$_3$.

20. A compound according to claim 17 wherein $R_{12}$ is

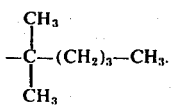

21. A compound according to claim 17 wherein $R_{12}$ is

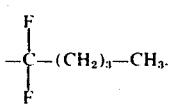

22. A compound according to claim 17 wherein $R_{12}$ is

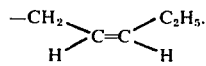

23. A compound according to claim 17 wherein $R_{12}$ is

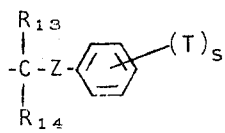

wherein $R_{13}$ and $R_{14}$ are hydrogen, alkyl of 1 to 4 carbon atoms, inclusive, or fluoro, being the same or different, with the proviso that $R_{13}$ is fluoro only when $R_{14}$ is hydrogen or fluoro; wherein T is alkyl of one to 4 carbon atoms, inclusive, fluoro, chloro, trifluoromethyl, or —$OR_{15}$, wherein $R_{15}$ is hydrogen or alkyl of 1 to 4 carbon atoms, inclusive, and s is zero, 1, 2, or 3, with the proviso that not more than two T's are other than alkyl; and wherein Z represents an oxa atom (—O—) or $C_jH_{2j}$, wherein $C_jH_{2j}$ is a valence bond or alkylene of 1 to 9 carbon atoms, inclusive, substituted with zero, one, or 2 fluoro, with 1 to 6 carbon atoms, inclusive, between —$CR_{13}R_{14}$— and the ring.

24. A compound according to claim 23 wherein Z is an oxa atom.

25. A compound according to claim 24 wherein $R_{13}$ and $R_{14}$ are hydrogen and s is zero.

26. A compound according to claim 23 wherein Z is methylene.

27. An optically active compound of the formula

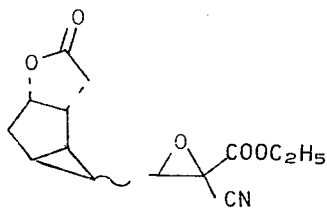

or a mixture of that compound and the enantiomer thereof wherein ~ indicates attachment in endo or exo configuration.

28. An optically active compound according to claim 27.

29. An optically active compound of the formula

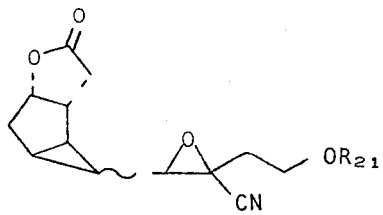

or a mixture of that compound and the enantiomer thereof wherein $R_{21}$ is
1. $R_{16}$, defined as 1-ethoxyethyl, tetrahydropyranyl, tetrahydrofuranyl, or a group of the formula

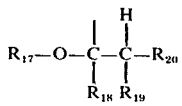

wherein $R_{17}$ is alkyl of 1 to 17 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of 1 to 4 carbon atoms, inclusive, wherein $R_{18}$ and $R_{19}$ are the same or different, being hydrogen, alkyl of 1 to 4 carbon atoms, inclusive, phenyl or phenyl substituted with one, 2, or 3 alkyl of 1 to 4 carbon atoms, inclusive, or, when $R_{18}$ and $R_{19}$ are taken together, —$(CH_2)_a$— or —$(CH_2)_b$—O—$(CH_2)_c$— wherein a is 3, 4, or 5, b is 1, 2, or 3, and c is 1, 2, or 3 with the proviso that b plus c is 2, 3, or 4, and wherein $R_{20}$ is hydrogen or phenyl; or
2. carboxyacyl —$C(O)R_{22}$ wherein $R_{22}$ is hydrogen or alkyl of one to 17 carbon atoms, inclusive, and wherein ~ indicates attachment to the cyclopropane ring in endo or exo configuration.

30. An optically active compound according to claim 29.

31. An optically active compound of the formula

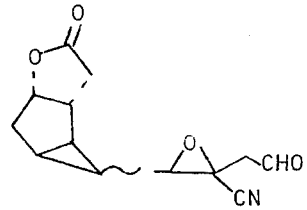

or a mixture of that compound and the enantiomer thereof wherein ~ indicates attachment to the cyclopropane ring in endo or exo configuration.

32. An optically active compound according to claim 31.

* * * * *

UNITED STATES PATENT OFFICE
CERTIFICATE OF CORRECTION

Patent No. 3,974,146             Dated  10 August 1976

Inventor(s)  David R. White

It is certified that error appears in the above-identified patent and that said Letters Patent are hereby corrected as shown below:

Face page, title , "CYANOLPOXY" should read -- CYANOEPOXY --.
Column 1, line 1, "CYANOLPOXY" should read -- CYANOEPOXY --.
Column 13, line 18, "usefl" should read -- useful --.
Column 18, line 39, "and $R_{19}$ are taken together" should read -- and $R_{19}$ are the same or different, being, hydrogen, alkyl of one to 4 carbon atoms, inclusive, phenyl or phenyl substituted with one, 2, or 3 alkyl of one to 4 carbon atoms, inclusive, or, when $R_{18}$ and $R_{19}$ are taken together --.
Column 18, line 44, "$-C(O)R_{(o)R22}$" should read -- $-C(O)R_{22}$ --.

Column 19, line 64, "-methylhexanenitirle" should read -- -methylhexanenitrile --.
Column 24, line 36, "of 31 10° to 0°" should read -- of -10 to 0° --.
Column 25, line 20, ", 6.3," should read -- , 6.2, --.
Column 25, line 31, "$PGF_2$" should read -- $PGF_2\alpha$ --.
Column 27, line 45, "$-PGF_2$" should read -- $-PGF_2\alpha$ --.
Column 27, line 54, "$PGF_2$" should read -- $PGF_2\alpha$ --.
Column 27, line 65, "-1-pentyl)" should read -- -1-pentenyl) --.
Column 30, line 27, "queous" should read -- aqueous --.
Column 31, line 10, " ito" should read -- into --.
Column 31, line 16, "cynohydrin" should read -- cyanohydrin --.

Signed and Sealed this

Twenty-eighth Day of July 1981

[SEAL]

Attest:

GERALD J. MOSSINGHOFF

Attesting Officer      Commissioner of Patents and Trademarks